(12) United States Patent  
Okuda et al.

(10) Patent No.: US 11,894,133 B2  
(45) Date of Patent: Feb. 6, 2024

(54) PHARMACEUTICAL STORAGE BOX

(71) Applicant: PHC HOLDINGS CORPORATION, Tokyo (JP)

(72) Inventors: Akinobu Okuda, Nara (JP); Hideyuki Morii, Ehime (JP); Susumu Takagi, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 492 days.

(21) Appl. No.: 17/164,563

(22) Filed: Feb. 1, 2021

(65) Prior Publication Data

US 2021/0158954 A1  May 27, 2021

Related U.S. Application Data

(63) Continuation of application No. PCT/JP2019/023420, filed on Jun. 13, 2019.

(30) Foreign Application Priority Data

Aug. 3, 2018 (JP) .................................. 2018-146382

(51) Int. Cl.
*G06Q 30/00* (2023.01)
*G16H 40/40* (2018.01)
(Continued)

(52) U.S. Cl.
CPC ............. *G16H 40/40* (2018.01); *F25D 25/02* (2013.01); *F25D 29/00* (2013.01);
(Continued)

(58) Field of Classification Search
CPC ......... G06K 19/0723; G06K 19/07749; G06K 19/07773; G06K 7/10366; G06K 7/10158; G16H 20/13; G16H 40/20; G16H 40/40; F25D 2700/08; F25D 2325/021; F25D 2700/06
(Continued)

(56) References Cited

U.S. PATENT DOCUMENTS

2006/0000225 A1   1/2006   Locher
2006/0028392 A1   2/2006   Coveley
(Continued)

FOREIGN PATENT DOCUMENTS

CN      1783108 A      6/2006
EP      1 049 042 A1   11/2000
(Continued)

OTHER PUBLICATIONS

Chinese Office Action dated Jun. 9, 2022 issued in the corresponding Chinese Patent Application No. 201980047678.6, with English translation.
(Continued)

*Primary Examiner* — Daniel St Cyr
(74) *Attorney, Agent, or Firm* — Rimon P.C.

(57) ABSTRACT

A pharmaceutical storage box to be stored in a pharmaceutical refrigerator and managed by a controller, the pharmaceutical storage box includes: a storage portion to store a pharmaceutical, the pharmaceutical having an IC tag attached thereto; and an antenna configured to receive information of the IC tag.

24 Claims, 30 Drawing Sheets

(51) Int. Cl.
  *F25D 25/02* (2006.01)
  *F25D 29/00* (2006.01)
  *G06K 7/10* (2006.01)
  *B65D 25/06* (2006.01)
  *B65D 21/08* (2006.01)

(52) U.S. Cl.
  CPC ........ *G06K 7/10356* (2013.01); *B65D 21/086* (2013.01); *B65D 25/06* (2013.01); *F25D 2325/021* (2013.01); *F25D 2700/06* (2013.01)

(58) Field of Classification Search
  USPC .......................................... 235/385, 380, 492
  See application file for complete search history.

(56) References Cited

U.S. PATENT DOCUMENTS

| 2006/0125639 | A1 | 6/2006 | Jung et al. |
| 2007/0272746 | A1 | 11/2007 | Ortiz et al. |
| 2008/0284604 | A1 | 11/2008 | Rubinstein |
| 2014/0244289 | A1 | 8/2014 | Lowenstein |
| 2018/0372398 | A1* | 12/2018 | Cosgrove ............. G06Q 20/208 |
| 2019/0340855 | A1* | 11/2019 | Clouser ............. G07C 9/00182 |

FOREIGN PATENT DOCUMENTS

| JP | H11-180513 A | 7/1999 |
| JP | 2000-105149 A | 4/2000 |
| JP | 2001-026308 A | 1/2001 |
| JP | 2002-068167 A | 3/2002 |
| JP | 2002-154617 A | 5/2002 |
| JP | 2003-072919 A | 3/2003 |
| JP | 2007-304866 A | 11/2007 |
| JP | 2007-326653 A | 12/2007 |
| JP | 2010-207376 A | 9/2010 |
| JP | 2011-027275 A | 2/2011 |
| JP | 3199697 U | 9/2015 |
| JP | 2016-201085 A | 12/2016 |

OTHER PUBLICATIONS

European Office Action dated Jun. 28, 2022 issued in the corresponding European Patent Application No. 19844012.5.
European Office Action dated Nov. 3, 2022 issued in the corresponding European Patent Application No. 19844012.5.
Notice of Reasons for Refusal dated Jun. 7, 2022 issued in the corresponding Japanese Patent Application No. 2020-534087, with English translation.
European Office Action dated Feb. 15, 2022 issued in the corresponding European Patent Application No. 19844012.5.
Extended European Search Report issued in European Patent Application No. 19844012.5, dated Aug. 6, 2021.
International Search Report issued in International Patent Application No. PCT/JP2019/023420, dated Aug. 27, 2019; with English translation.
Notice of Reasons for Refusal issued in Japanese Patent Application No. 2020-534087, dated Nov. 30, 2021; with English translation.
First Office Action issued in Chinese Patent Application No. 201980047678.6, dated Nov. 26, 2021; with English translation.

* cited by examiner

PHARMACEUTICAL STORAGE BOX

CROSS-REFERENCE TO RELATED APPLICATIONS

This is a continuation application of International Patent Application No. PCT/JP2019/023420 filed Jun. 13, 2019, which claims the benefit of priority to Japanese Patent Application No. 2018-146382 filed Aug. 3, 2018, the entire contents of each of which the entire contents of each of which are incorporated herein by reference.

BACKGROUND

Technical Field

The present disclosure relates to a pharmaceutical storage box.

Description of the Related Art

For example, pharmaceutical refrigerators to store pharmaceuticals in an environment at a predetermined storage temperature are known (for example, see Japanese Patent Application Publication No. 2000-105149).

In an actual situation, the pharmaceuticals in the pharmaceutical refrigerator are placed in an environment at a predetermined storage temperature, however, information on putting-in and taking-out of the pharmaceuticals is not sufficiently managed. Accordingly, in a medical institution and/or the like, necessary and sufficient management of the pharmaceuticals may not be able to be performed.

Thus, the present disclosure is directed to provision of a general-purpose pharmaceutical storage box that is to be stored in a pharmaceutical refrigerator and that can manage information on putting-in and taking-out of pharmaceuticals, and the like.

SUMMARY

A primary aspect of the present disclosure is a pharmaceutical storage box to be stored in a pharmaceutical refrigerator and managed by a controller, the pharmaceutical storage box comprising: a storage portion to store a pharmaceutical, the pharmaceutical having an IC tag attached thereto; and an antenna configured to receive information of the IC tag.

Other features of the present disclosure will become apparent from the following description and the drawings.

According to the present disclosure, storing the pharmaceutical storage box in the pharmaceutical refrigerator enables management of information on such as putting-in and taking-out of a pharmaceuticals, and the like.

DETAILED DESCRIPTION

At least following matters will be apparent from the description of the present specification and the accompanying drawings.

===Pharmaceutical Refrigerator===

Figure 1:
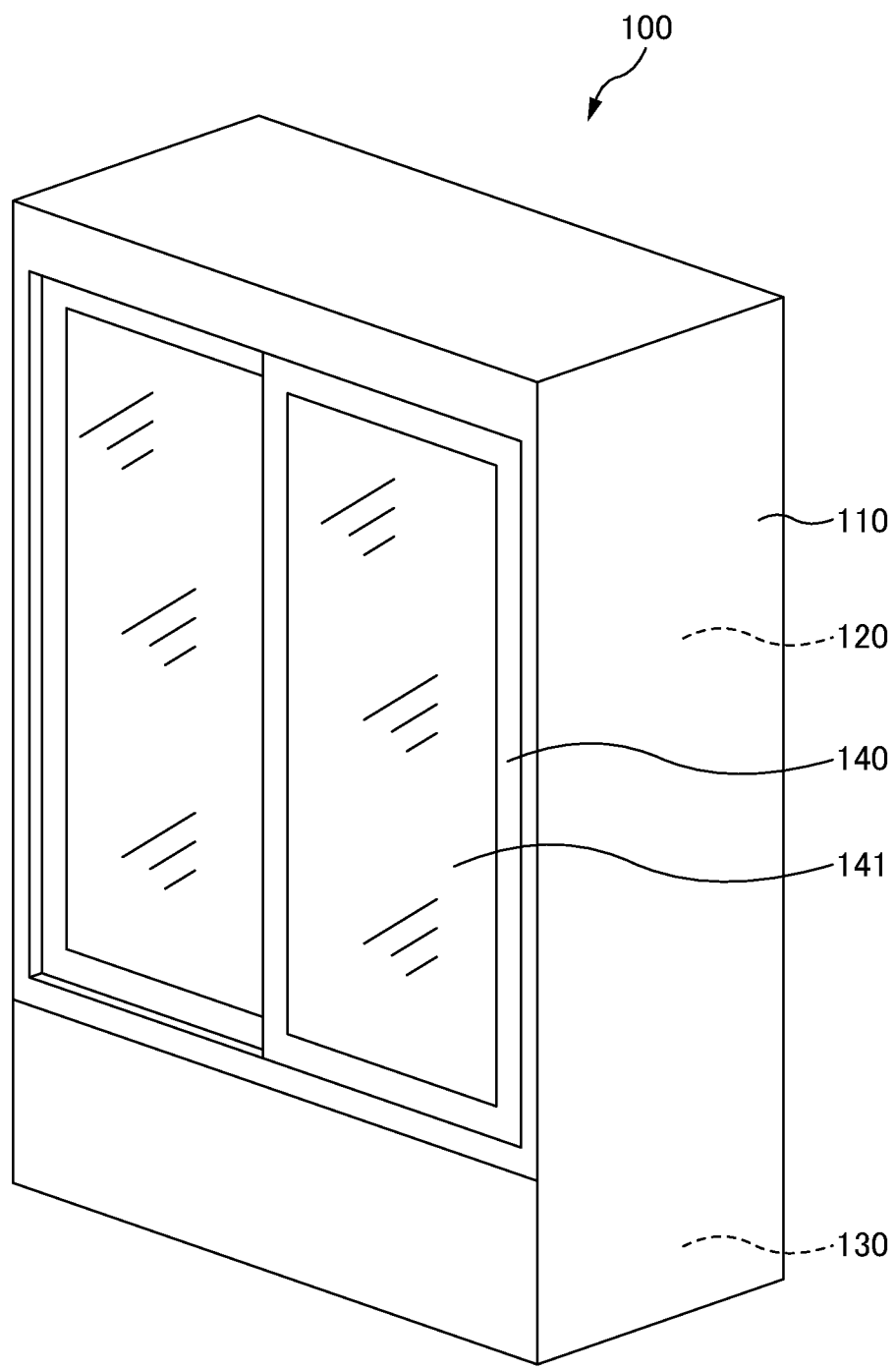
FIG. 1 is a perspective view illustrating an example of a pharmaceutical refrigerator in which a pharmaceutical storage box according to an embodiment of the present disclosure is to be stored.
Figure 2:
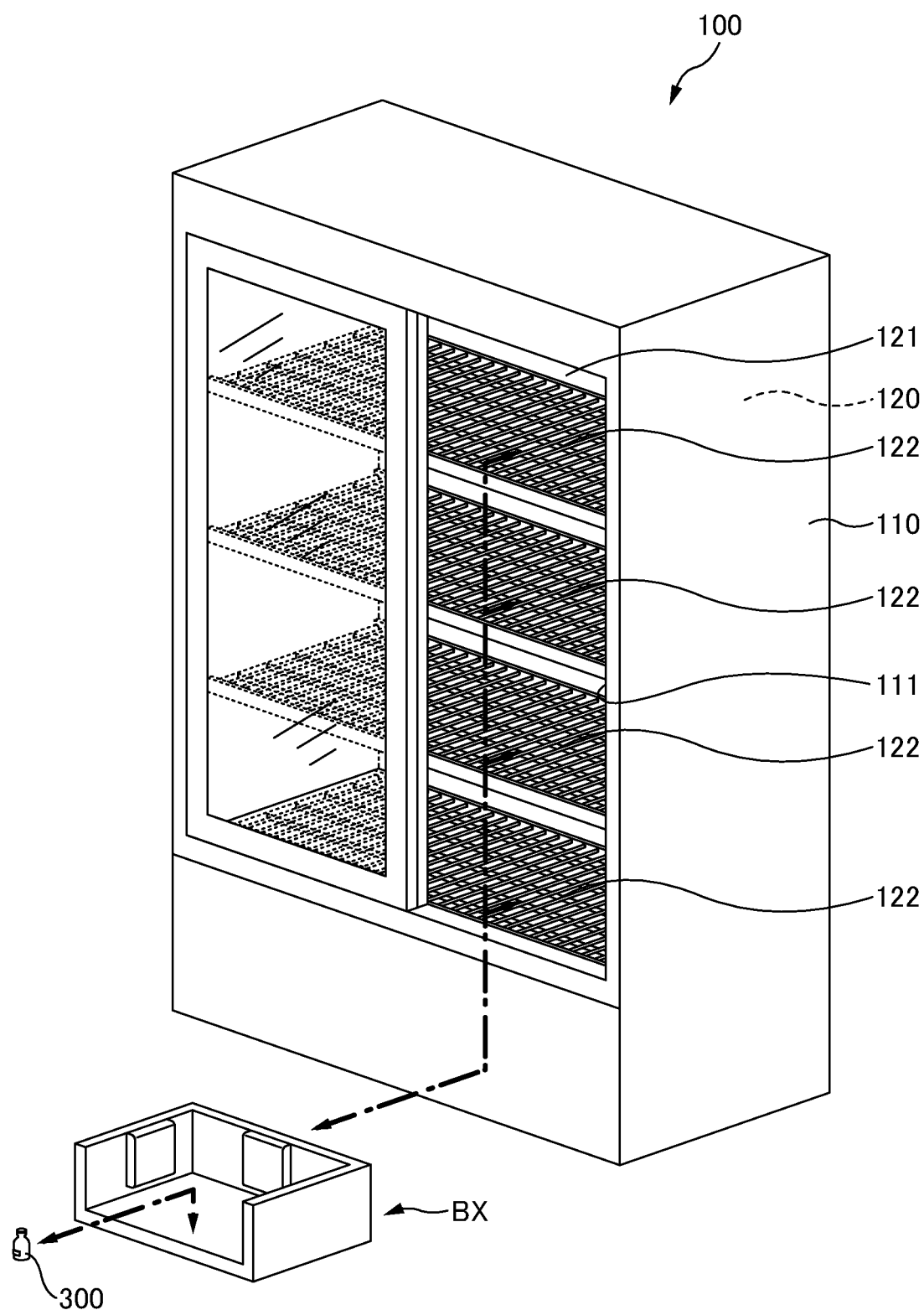
FIG. 2 is a perspective view illustrating how a pharmaceutical storage box according to an embodiment of the present disclosure is taken in and out of a pharmaceutical refrigerator of FIG. 1.

FIG. 1 is a perspective view illustrating an example of a pharmaceutical refrigerator in which a pharmaceutical storage box according to an embodiment of the present disclosure is to be stored. FIG. 2 is a perspective view illustrating how the pharmaceutical storage box according to an embodiment of the present disclosure is taken in and out of the pharmaceutical refrigerator of FIG. 1.

A pharmaceutical refrigerator 100 is an apparatus that is installed, for example, in a medical institution, and that stores pharmaceuticals (pharmaceutical products) of a pharmaceutical manufacturer provided via a pharmaceutical wholesaler, and refrigerates them at a predetermined temperature.

The pharmaceutical refrigerator 100 includes an outer case 110, an inner case 120, a machine room 130, and a door 140.

The outer case 110 has a rectangular cuboid shape and has an opening 111 on a front surface thereof for loading and unloading pharmaceuticals. The inner case 120 has a rectangular cuboid shape, has an opening 121 on a front surface thereof to communicate with the opening 111, and is provided in the outer case 110 with a heat insulating material provided between the inner case 120 and the outer case 110. Multiple shelves 122 are provided in the inner case 120 to store the pharmaceuticals. The shelves 122 have, for example, a mesh shape to allow air to pass therethrough. The machine room 130 is formed below the inner case 120 in the outer case 110 and a cooling device (not illustrated) that refrigerates the inside of the inner case 120 is provided. The cooling device circulates coolant by using, for example, a compressor, a condenser, an evaporator, and the like, and is coupled to the inner case 120 such that air at a predetermined refrigeration temperature circulates in the inner case 120. The door 140 has a glass window 141 for checking the inside of the inner case 120, and is slidably attached to the opening 111 of the outer case 110. Closing the door 140 causes the inside of the inner case 120 to be a closed space and enables refrigeration of the pharmaceuticals.

In an embodiment of the present disclosure, it is assumed that the pharmaceutical storage box for storing the pharmaceuticals to be managed is placed on one of the shelves 122 in the inner case 120 of the pharmaceutical refrigerator 100 so as to be insertably removable from the pharmaceutical refrigerator through the openings 111, 121. The pharmaceutical storage box will be described later in detail.

===Pharmaceutical Storage Box===

First Example

Figure 3:
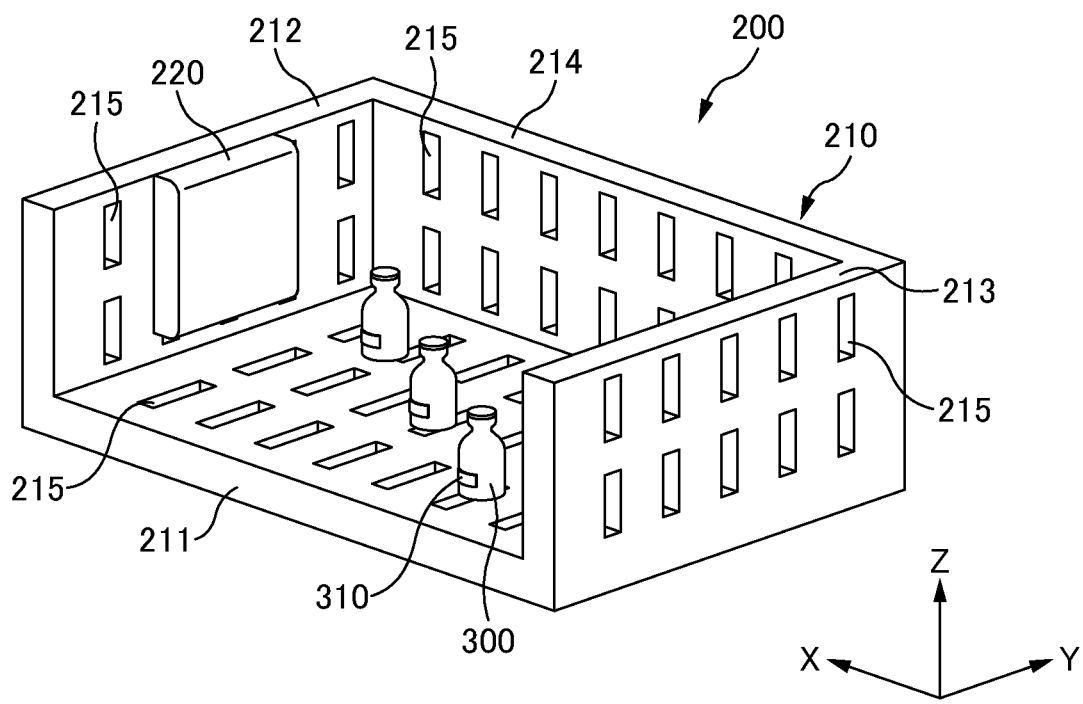
FIG. 3 is a perspective view illustrating an example (first example) of a pharmaceutical storage box according to an embodiment of the present disclosure.

FIG. 3 is a perspective view illustrating an example of the pharmaceutical storage box according to an embodiment of the present disclosure. In FIG. 3, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 200 is a box for storing pharmaceuticals 300 to be managed.

The pharmaceutical storage box 200 includes a storage portion 210 and an antenna 220.

The storage portion 210 is defined by a total of four flat plates of a bottom plate 211, side plates 212, 213, and a back plate 214. The storage portion 210 may be formed, for example, such that the bottom plate 211, the side plates 212, 213, and the back plate 214 are integrally formed by die molding using a resin material. Alternatively, the storage portion 210 may be formed, for example, such that the bottom plate 211, the side plates 212, 213, and the back plate 214 are separately formed by die molding using a resin material, and then the bottom plate 211, the side plates 212, 213, and the back plate 214 are bonded to one another with adhesive and/or the like. The storage portion 210 has multiple air passage holes 215 in each of the bottom plate 211, the side plates 212, 213, and the back plate 214 such that the pharmaceuticals 300 stored in the storage portion 210 are effectively refrigerated by the air circulating in the inner case 120.

An IC tag 310 for identifying the pharmaceutical 300 is attached to each pharmaceutical 300. In an embodiment of the present disclosure, it is assumed that the IC tag 310 is a passive RFIC tag including a loop coil and an IC chip, for example. ID information (product name, manufacturer code, expiration date, and the like) indicating the pharmaceutical 300 is stored in the IC chip in advance.

The antenna 220 is a device configured to transmit a radio wave in the storage portion 210 to activate the IC chip in the IC tag 310 attached to each pharmaceutical 300, and receive the ID information indicating the pharmaceutical 300. The ID information received by the antenna 220 is managed, by a controller described later, in association with information on a refrigeration temperature and put-in and take-out time points of the pharmaceutical 300. The antenna 220 has a flat plate shape and is attached to, for example, a surface of the side plate 212 facing the side plate 213.

Storing the pharmaceuticals 300 in the pharmaceutical storage box 200 and storing the pharmaceutical storage box 200 in the pharmaceutical refrigerator 100 enables management of the pharmaceuticals 300 and the pharmaceutical storage box 200 storing the pharmaceuticals 300. In addition, the pharmaceutical storage box 200 is associated with the antenna 220, which enables identification of the pharmaceutical storage box 200. Thus, it is also possible to manage the pharmaceuticals 300 and the pharmaceutical storage boxes 200 storing the pharmaceuticals 300 such that the pharmaceuticals 300 are sorted according to their types, pharmaceutical wholesalers, pharmaceutical manufacturers, and/or the like, and separately stored in multiple pharmaceutical storage boxes 200, and then the multiple pharmaceutical storage boxes 200 are stored in the pharmaceutical refrigerator 100. In addition, a pharmaceutical refrigerator 100 already installed in a medical institution or the like can also be used to store the pharmaceutical storage boxes 200.

Second Example

Figure 4:
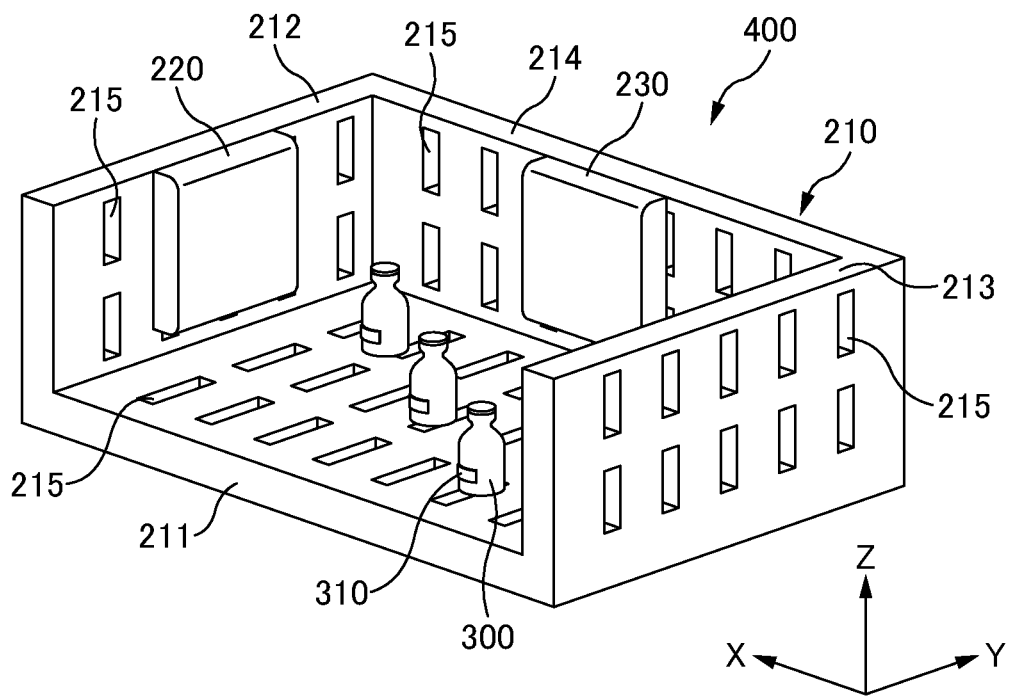
FIG. 4 is a perspective view illustrating another example (second example) of a pharmaceutical storage box according to an embodiment of the present disclosure.
Figure 5:
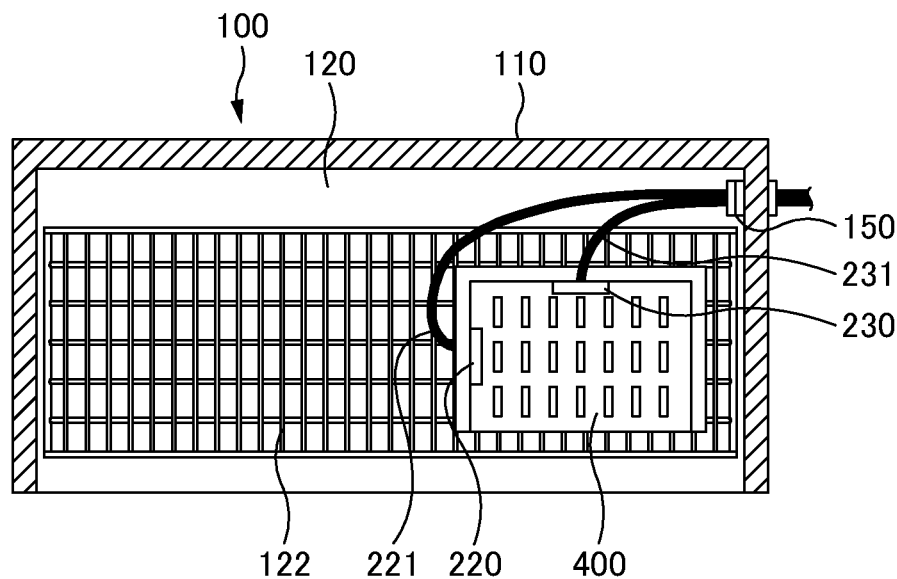
FIG. 5 is a plan view illustrating an example of a coupling portion for leading out a coupling line of an antenna in a pharmaceutical storage box according to an embodiment of the present disclosure.

FIG. 4 is a perspective view illustrating another example of the pharmaceutical storage box according to an embodiment of the present disclosure. In FIG. 4, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box. FIG. 5 is a plan view illustrating an example of a coupling portion for leading out a coupling line of an antenna in the pharmaceutical storage box according to an embodiment of the present disclosure. Note that, in the second example, the same components as those in the first example are denoted by the same reference numerals and description thereof is omitted.

A pharmaceutical storage box 400 is a box for storing the pharmaceuticals 300 to be managed.

The pharmaceutical storage box 400 includes the storage portion 210 and antennas 220, 230.

The antennas 220, 230 are devices configured to transmit radio waves in the storage portion 210 to activate the IC chip in the IC tag 310 attached to each pharmaceutical 300, and receive the ID information indicating the pharmaceutical 300. The ID information received by the antennas 220, 230 is managed, by the controller described later, in association with the information on the refrigeration temperature and the put-in and take-out time points of the pharmaceutical 300.

In the first example, when the pharmaceutical 300 is stored in the pharmaceutical storage box 200 such that the surface of the IC tag 310 is positioned perpendicular to the surface of the antenna 220 facing the side plate 213, the radio wave transmitted from the antenna 220 and the loop coil in the IC tag 310 may not be interlinked, and thus the antenna 220 may not correctly receive the ID information indicating the pharmaceutical 300 from the IC chip in the IC tag 310 thereof. Specifically, when the pharmaceutical 300 is stored in the pharmaceutical storage box 200 such that the surface of the IC tag 310 is along a plane formed by the X-axis and the Z-axis, the surface (surface extending along the plane formed by the X-axis and the Z-axis) of the IC tag 310 is positioned perpendicular to the surface (surface extending along a plane formed by the Y-axis and the Z-axis) of the antenna 220 facing the side surface 213, and thus the antenna 220 may not correctly receive the ID information indicating the pharmaceutical 300 from the IC chip in the IC tag 310 thereof. For example, when the pharmaceutical 300 is enclosed in a vial and the IC tag 310 is attached to a side surface of the vial, the aforementioned issue becomes outstanding.

Thus, the antenna 230 having a flat plate shape is attached to a surface of the back plate 214 between the side plates 212 and 213. This establishes a positional relationship that the surface (surface extending along the plane formed by the Y-axis and the Z-axis) of the antenna 220 is perpendicular to the surface (surface extending along the plane formed by the X-axis and the Z-axis) of the antenna 230. Accordingly, the antennas 220, 230 can correctly receive the ID information indicating each pharmaceutical 300 from the IC chip in the IC tag 310 thereof, regardless of the direction in which the pharmaceutical 300 is stored about the Z-axis.

A coupling line (communication line) 221 of the antenna 220 and a coupling line (communication line) 231 of the antenna 230 are, for example, coupled to an external controller via a connector 150 provided at a corner on the rear side of the pharmaceutical refrigerator 100 so as not to hinder putting-in and taking-out of the pharmaceutical storage box 400. The pharmaceutical storage box 400 can be easily taken in and out by plugging and unplugging the connector 150.

Third Example

Figure 6:
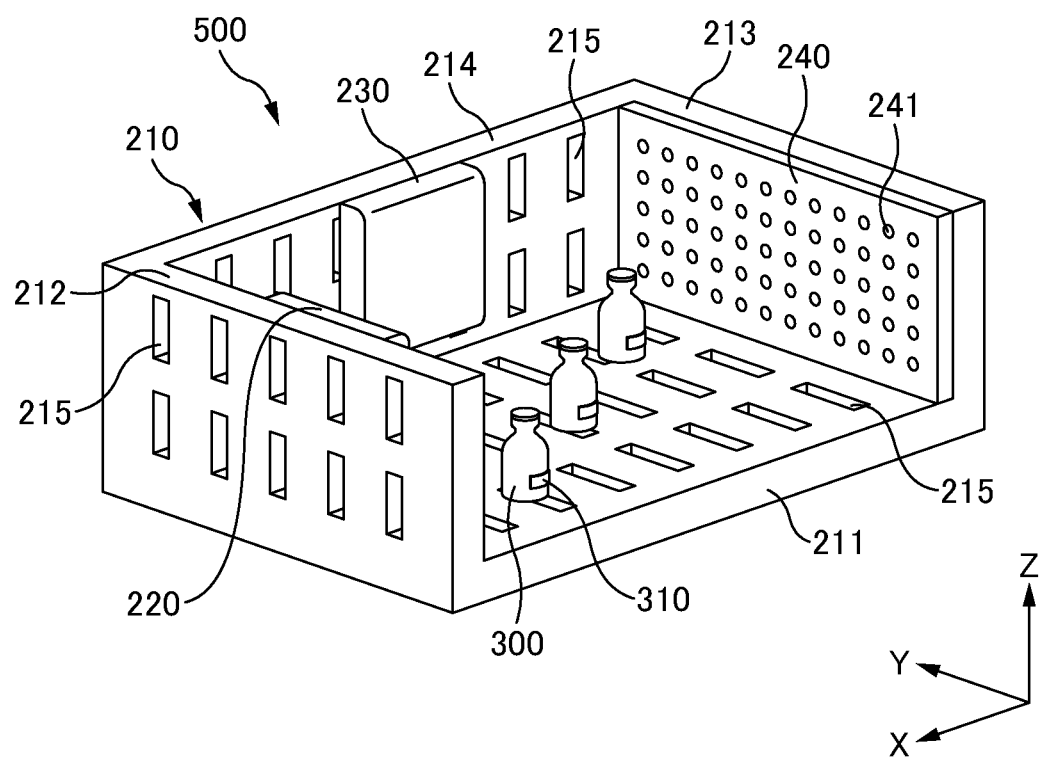
FIG. 6 is a perspective view illustrating another example (third example) of a pharmaceutical storage box according to an embodiment of the present disclosure.

FIG. 6 is a perspective view illustrating another example of the pharmaceutical storage box according to an embodiment of the present disclosure. In FIG. 6, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box. Note that, in the third example, the same components as those in the second example are denoted by the same reference numerals and description thereof is omitted.

A pharmaceutical storage box 500 is a box for storing the pharmaceuticals 300 to be managed.

The pharmaceutical storage box 500 includes the storage portion 210, the antennas 220, 230, and a shielding plate 240.

The shielding plate 240 is a metal plate that reflects the radio waves transmitted from the antennas 220, 230. The shielding plate 240 is attached to, for example, a surface (surface to which neither of the antennas 220 nor 230 is attached) of the side plate 213 facing the side plate 212. Multiple small-diameter recesses 241 are formed on a surface of the shielding plate 240 facing the side plate 212. The recesses 241 diffusely reflect the radio waves transmitted from the antennas 220, 230, thereby being able to enhance the possibility that the radio waves transmitted from the antennas 220, 230 and the loop coil in the IC tag 310 are interlinked.

Although the shielding plate 240 is attached to the side plate 213, the side plate 213 itself may be the shielding plate 240.

Fourth Example

Figure 7:
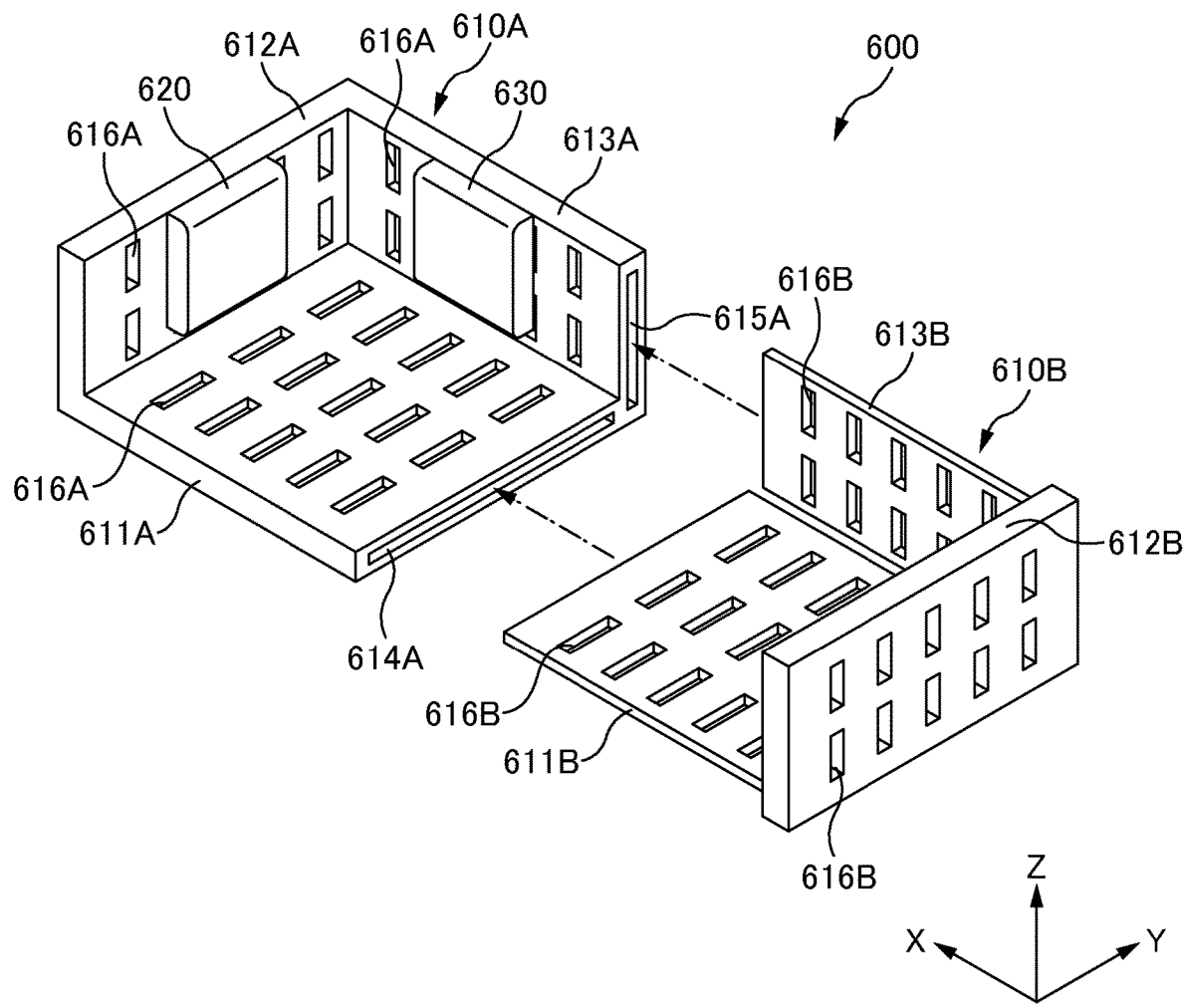
FIG. 7 is an exploded perspective view illustrating another example (fourth example) of a pharmaceutical storage box according to an embodiment of the present disclosure.
Figure 8:
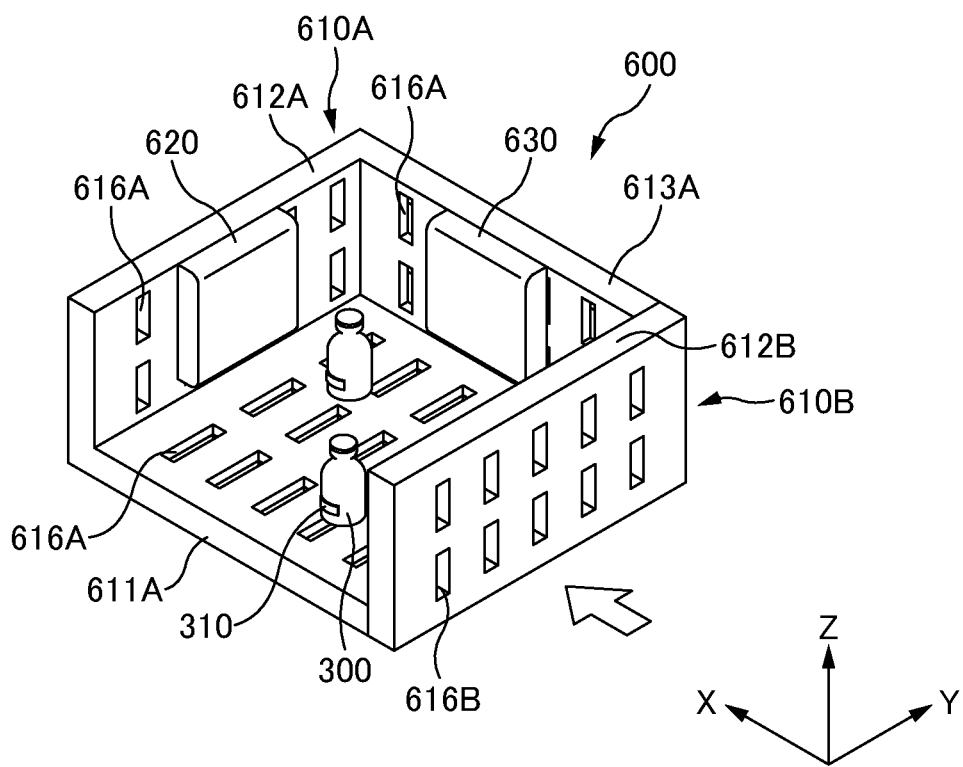
FIG. 8 is a perspective view illustrating a state in which the width of a pharmaceutical storage box in FIG. 7 is reduced.
Figure 9:
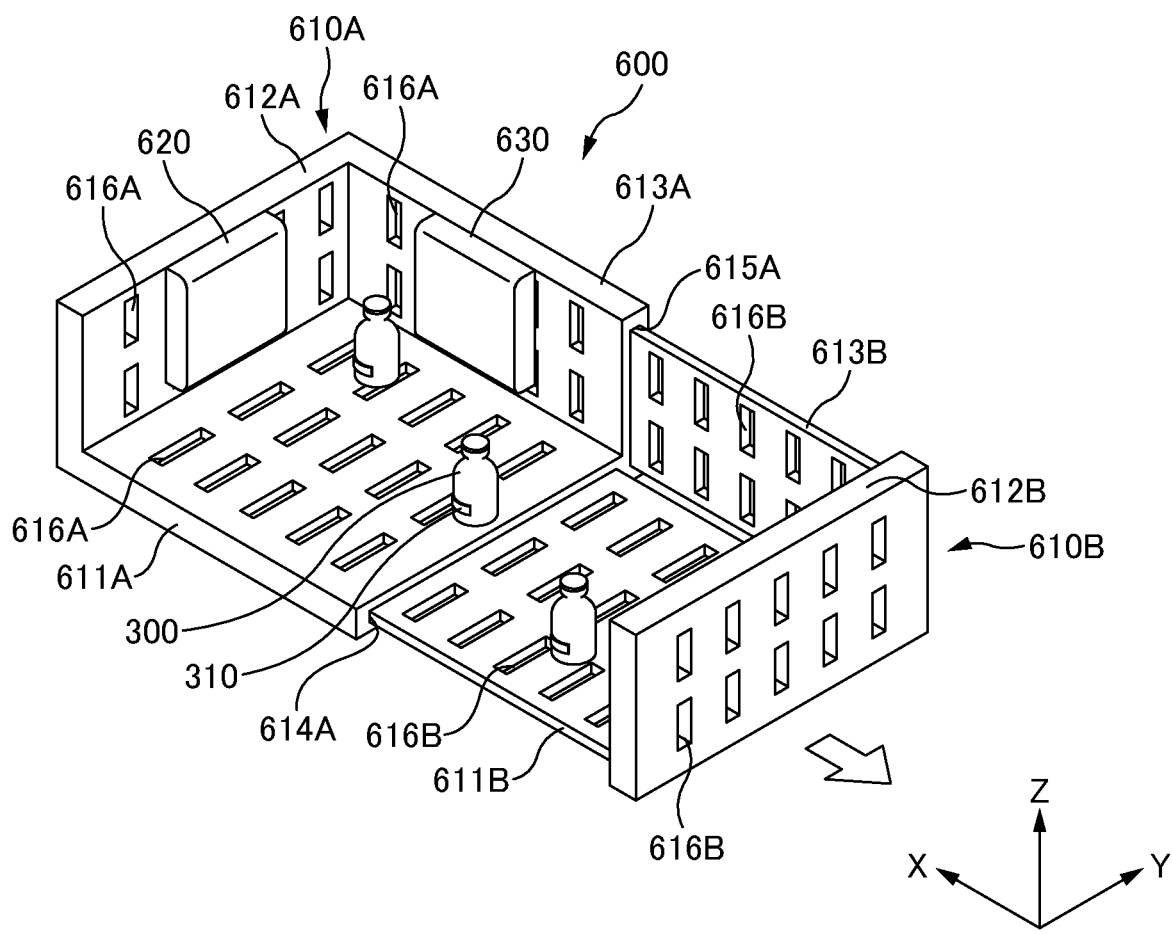
FIG. 9 is a perspective view illustrating a state in which the width of a pharmaceutical storage box illustrated in FIG. 7 is increased.

FIG. 7 is an exploded perspective view illustrating another example of the pharmaceutical storage box according to an embodiment of the present disclosure. FIG. 8 is a perspective view illustrating a state in which the width of the pharmaceutical storage box illustrated in FIG. 7 is reduced. FIG. 9 is a perspective view illustrating a state in which the width of the pharmaceutical storage box illustrated in FIG. 7 is increased. In FIGS. 7 to 9, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 600 is a box for storing the pharmaceuticals 300 to be managed.

The pharmaceutical storage box 600 is configured such that the width (in the direction along the X-axis) thereof can change according to the volume of the inside of the inner case 120, the number of pharmaceutical storage boxes to be stored in the inner case 120, and the like.

The pharmaceutical storage box 600 includes a storage portion 610 and antennas 620, 630.

The storage portion 610 is formed such that a first storage portion 610A and a second storage portion 610B are combined so as to change the width (change of the volume) of the pharmaceutical storage box 600.

The first storage portion 610A is defined by a total of three flat plates of a bottom plate 611A, a side plate 612A, and a back plate 613A. The bottom plate 611A has a groove 614A in which the second storage portion 610B is slidable along the X-axis and the back plate 613A has a groove 615A in which the second storage portion 610B is slidable along the X-axis. The first storage portion 610A may be formed, for example, such that the bottom plate 611A, the side plate 612A, and the back plate 613A are integrally formed by die molding using a resin material. Alternatively, the first storage portion 610A may be formed, for example, such that the bottom plate 611A, the side plate 612A, and the back plate 613A are separately formed by die molding using a resin material, and then the bottom plate 611A, the side plate 612A, and the back plate 613A are bonded to one another with adhesive and/or the like.

The second storage portion 610B is defined by a total of three flat plates of a bottom plate 611B, a side plate 612B, and a back plate 613B. The bottom plate 611B is inserted into the groove 614A so as to slide inside the groove 614A, and the back plate 613B is inserted into the groove 615A so as to slide inside the groove 615A. The second storage portion 610B may be formed, for example, such that the bottom plate 611B, the side plate 612B, and the back plate 613B are integrally formed by die molding using a resin material. Alternatively, the second storage portion 610B may be formed, for example, such that the bottom plate 611B, the side plate 612B, and the back plate 613B are separately formed by die molding using a resin material, and then the bottom plate 611B, the side plate 612B, and the back plate 613B are bonded to one another with adhesive and/or the like.

As such, the storage portion 610 is formed such that the bottom plate 611B is inserted into the groove 614A of the bottom plate 611A and the back plate 613B is inserted into the groove 615A of the back plate 613A. Then, sliding the second storage portion 610B in a direction (−X direction) away from the first storage portion 610A increases the width of the storage portion 610, thereby increasing the volume of the storage portion 610. Meanwhile, sliding the second storage portion 610B in a direction (+X direction) toward the first storage portion 610A reduces the width of the storage portion 610, thereby reducing the volume of the storage portion 610.

The first storage portion 610A has multiple air passage holes 616A in each of the bottom plate 611A, the side plate 612A, and the back plate 613A such that the pharmaceuticals 300 stored in the storage portion 610 are effectively refrigerated by the air circulating in the inner case 120. The second storage portion 610B has multiple air passage holes 616B in each of the bottom plate 611B, the side plate 612B, and the back plate 613B such that the pharmaceuticals 300 stored in the storage portion 610 are effectively refrigerated by the air circulating in the inner case 120.

The antennas 620, 630 are devices configured to transmit radio waves in the storage portion 610 to activate the IC chip in the IC tag 310 attached to each pharmaceutical 300, and receive the ID information indicating the pharmaceutical 300. The ID information received by the antennas 620, 630 is managed, by the controller described later, in association with the information on the refrigeration temperature and the put-in and take-out time points of the pharmaceutical 300.

The antenna 620 having a flat plate shape is attached, for example, to a surface of the side plate 612A facing the side plate 612B. The antenna 630 having a flat plate shape is attached to a surface of the back plate 613A between the side plates 612A and 612B. This establishes a positional relationship that the surface (surface extending along a plane formed by the Y-axis and the Z-axis) of the antenna 620 is perpendicular to the surface (surface extending along a plane formed by the X-axis and the Z-axis) of the antenna 630. Accordingly, the antennas 620, 630 can correctly receive the ID information indicating each pharmaceutical 300 from the IC chip in the IC tag 310 thereof, regardless of the direction in which the pharmaceutical 300 is stored about the Z-axis.

Storing the pharmaceuticals 300 in the pharmaceutical storage box 600 and storing the pharmaceutical storage box 600 in the pharmaceutical refrigerator 100 enables management of the pharmaceuticals 300 and the pharmaceutical storage box 600 storing the pharmaceuticals 300. In addition, the pharmaceutical storage box 600 is associated with the antennas 620, 630, which enables identification of the pharmaceutical storage box 600. Thus, it is also possible to manage the pharmaceuticals 300 and the pharmaceutical storage boxes 600 storing the pharmaceuticals 300 such that the pharmaceuticals 300 are sorted according to their types, pharmaceutical wholesalers, pharmaceutical manufacturers, and/or the like, and separately stored in multiple pharmaceutical storage boxes 600, and then the multiple pharmaceutical storage boxes 600 are stored in the pharmaceutical refrigerator 100. In this case, it is possible to change the width of the pharmaceutical storage box 600 as appropriate according to the volume and/or shape of the pharmaceutical refrigerator 100 and effectively use the space inside the pharmaceutical refrigerator 100. In addition, it is also possible to use a pharmaceutical refrigerator 100 already installed in a medical institution or the like for storing the pharmaceutical storage boxes 600.

Although the case where the antenna 630 is attached to the surface of the back plate 613A between the side plates 612A and 612B is described in an example of the present disclosure, the present disclosure is not limited thereto. The antenna 630 may be configured to be attachable also to a surface of the back plate 613B between the side plates 612A and 612B. In this case, the second storage portion 610B is slid in the direction away from (−X direction) or the direction toward (+X direction) the first storage portion 610A and then the antenna 630 is attached to a substantially center portion of the surface (surface of one of the back plates 613A and 613B) between the side plates 612A and 612B, thereby being able to evenly distribute the radio wave transmitted from the antenna 630 in the width direction (direction along the X-axis) of the pharmaceutical storage box 600.

Fifth Example

Figure 10:
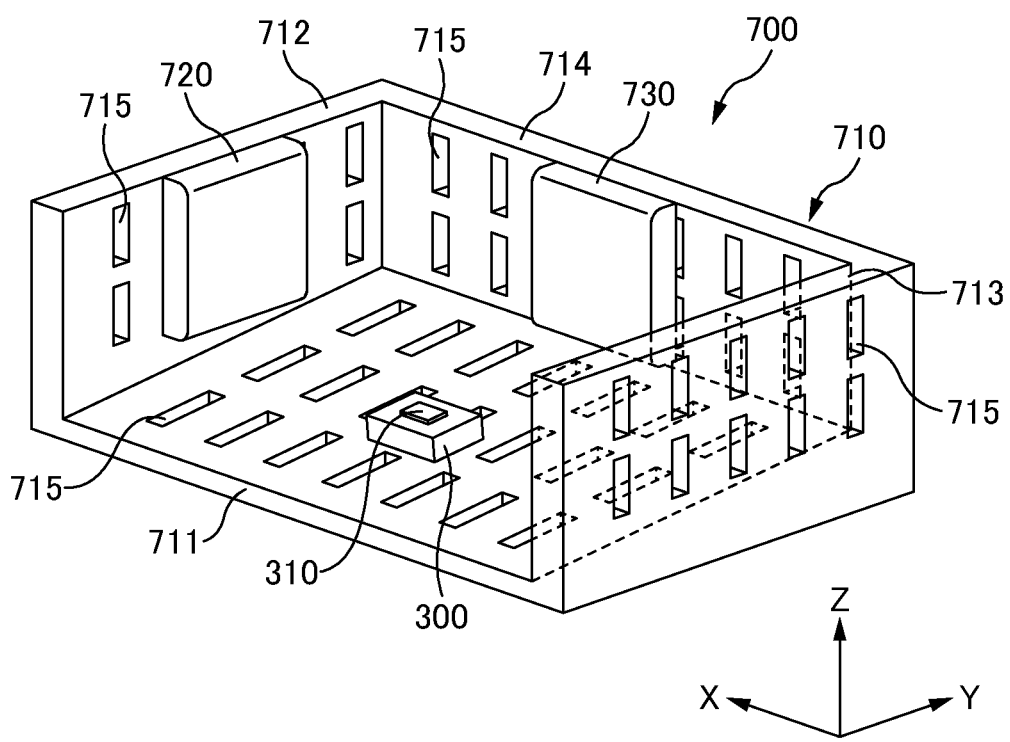
FIG. 10 is a perspective view illustrating another example (fifth example) of a pharmaceutical storage box according to an embodiment of the present disclosure.

FIG. 10 is a perspective view illustrating another example of the pharmaceutical storage box according to an embodiment of the present disclosure. In FIG. 10, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 700 is a box for storing the pharmaceuticals 300 to be managed.

The pharmaceutical storage box 700 includes a storage portion 710 and antennas 720, 730.

The storage portion 710 is defined by a total of four flat plates of a bottom plate 711, side plates 712, 713, and a back plate 714. The surface of the bottom plate 711 on which the pharmaceuticals 300 are to be placed is tilted downward (toward a −Z direction) as it extends away from the back plate 714 (toward a −Y direction).

The storage portion 710 may be formed, for example, such that the bottom plate 711, the side plates 712, 713, and the back plate 714 are integrally formed by die molding using a resin material. Alternatively, the storage portion 710 may be formed, for example, such that the bottom plate 711, the side plates 712, 713, and the back plate 714 are separately formed by die molding using a resin material and then the bottom plate 711, the side plates 712, 713, and the back plate 714 are bonded to one another with adhesive and/or the like. The storage portion 710 has multiple air passage holes 715 in each of the bottom plate 711, the side plates 712, 713, and the back plate 714 such that the pharmaceuticals 300 stored in the storage portion 710 are effectively refrigerated by the air circulating in the inner case 120.

The antennas 720, 730 are devices configured to transmit radio waves in the storage portion 710 to activate the IC chip in the IC tag 310 attached to each pharmaceutical 300, and receive the ID information indicating the pharmaceutical 300. The ID information received by the antennas 720, 730 is managed, by the controller described later, in association with the information on the refrigeration temperature and the put-in and take-out time points of the pharmaceutical 300.

The antenna 720 having a flat plate shape is attached to, for example, a surface of the side plate 712 facing the side plate 713. The antenna 730 having a flat plate shape is attached to a surface of the back plate 714 between the side plates 712 and 713. The surface (surface extending along a plane formed by the Y-axis and the Z-axis) of the antenna 720 is perpendicular to the surface (surface extending along a plane formed by the X-axis and the Z-axis) of the antenna 730.

In the second example, when the pharmaceutical 300 is stored in the pharmaceutical storage box 200 such that the surface of the IC tag 310 is perpendicular to the surfaces of the antennas 220, 230, the radio waves transmitted from the antennas 220, 230 and the loop coil in the IC tag 310 may not be interlinked, and thus the antennas 220, 230 may not correctly receive the ID information indicating the pharmaceutical 300 from the IC chip in the IC tag 310 thereof. Specifically, when the pharmaceutical 300 is stored in the pharmaceutical storage box 200 such that the surface of the IC tag 310 is along a plane formed by the X-axis and the Y-axis, the surface (surface extending along the plane formed by the X-axis and the Y-axis) of the IC tag 310 results in being perpendicular to the surface (surface extending along the plane formed by the Y-axis and the Z-axis) of the antenna 220 and the surface (surface extending along the plane formed by the X-axis and the Z-axis) of the antenna 230. Thus, the antennas 220, 230 may not correctly receive the ID information indicating the pharmaceutical 300 from the IC chip in the IC tag 310 thereof. For example, assume a situation where the pharmaceutical 300 is enclosed in a rectangular cuboid case and the IC tag 310 is attached to one surface of the case. In this situation, when the pharmaceutical 300 is stored such that the surface to which the IC tag 310 is attached is positioned on the upper surface or the lower surface of the case, the aforementioned issue becomes outstanding.

Accordingly, the surface of the bottom plate 711 on which the pharmaceutical 300 is to be placed is tilted downward as it extends away from the back plate 714, so as not to be perpendicular to the surfaces of the antennas 720, 730. This enables the antennas 720, 730 to correctly receive the ID information indicating each pharmaceutical 300 from the IC chip in the IC tag 310 thereof, regardless of the direction in which the pharmaceutical 300 is stored.

The surface of the bottom plate 711 on which the pharmaceutical 300 is to be placed may be tilted downward (in the −Z direction) as it extends away from the side plate 712 (in the −X direction) or tilted downward (in the −Z direction) as it extends away from the side plate 713 (in the +X direction), instead of being tilted downward (in the −Z direction) as it extends away from the back plate 714 (in the −Y direction).

Sixth Example

Figure 11:
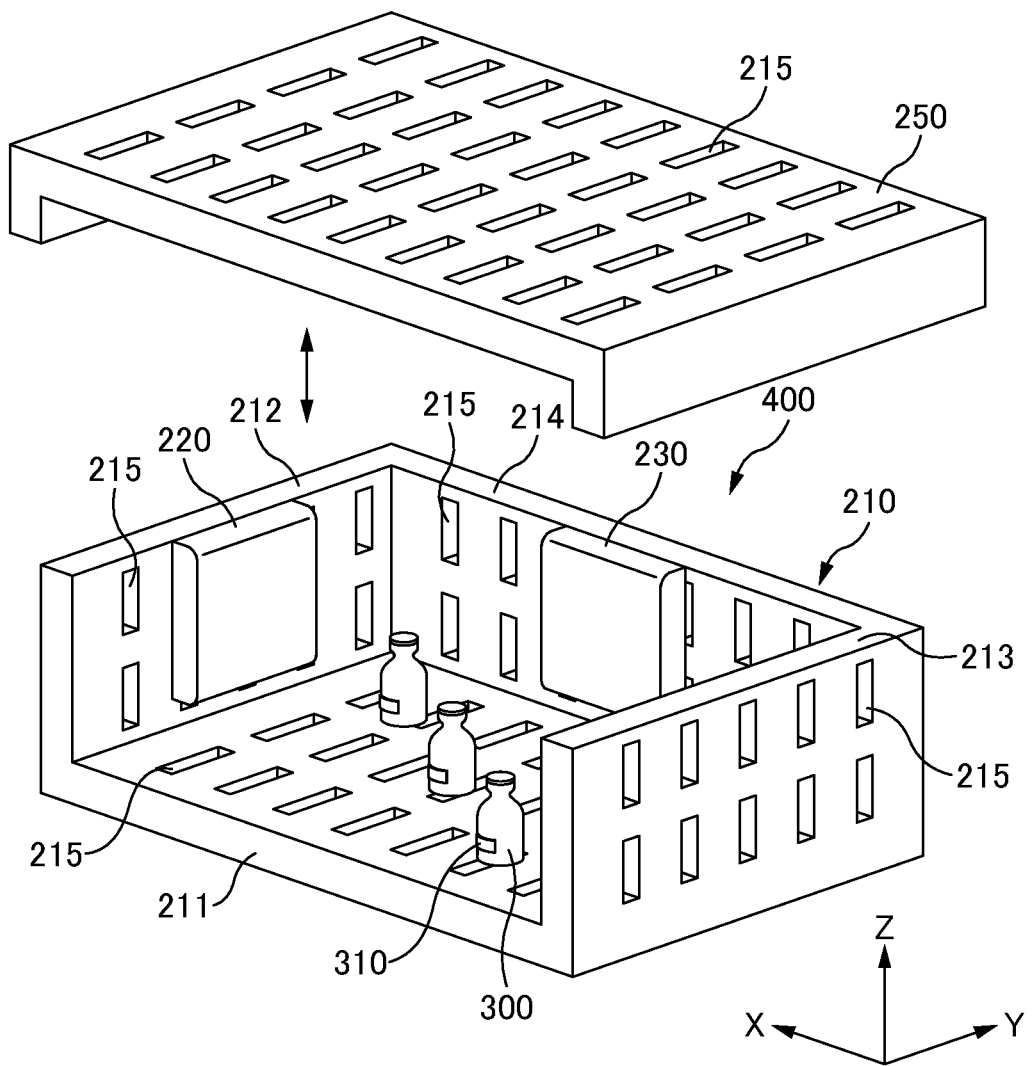
FIG. 11 is a perspective view illustrating another example (sixth example) of a pharmaceutical storage box according to an embodiment of the present disclosure.

FIG. 11 is a perspective view illustrating another example of the pharmaceutical storage box according to an embodiment of the present disclosure. In FIG. 11, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box. Note that, in the sixth example, the same components as those in the second example are denoted by the same reference numerals and description thereof is omitted.

The pharmaceutical storage box 400 has a top plate 250 that is detachably attachable to the storage portion 210.

The top plate 250 may be formed by die molding using a resin material or formed of a metal plate that reflects radio waves. The top plate 250 has multiple air passage holes 215 such that the pharmaceuticals 300 stored in the storage portion 210 are effectively refrigerated by the air circulating in the inner case 120 when the top plate 250 is attached to the storage portion 210.

Attaching the top plate 250 to the storage portion 210 can protect the pharmaceuticals 300 stored in the storage portion 210 while securing passage of air in the storage portion 210. In addition, it is possible to remove the top plate 250 from the storage portion 210, thereby being able to easily load and unload the pharmaceuticals 300.

Note that the top plate 250 is detachably attachable to all the pharmaceutical storage boxes disclosed in an embodiment of the present disclosure.

Seventh Example

Figure 12:
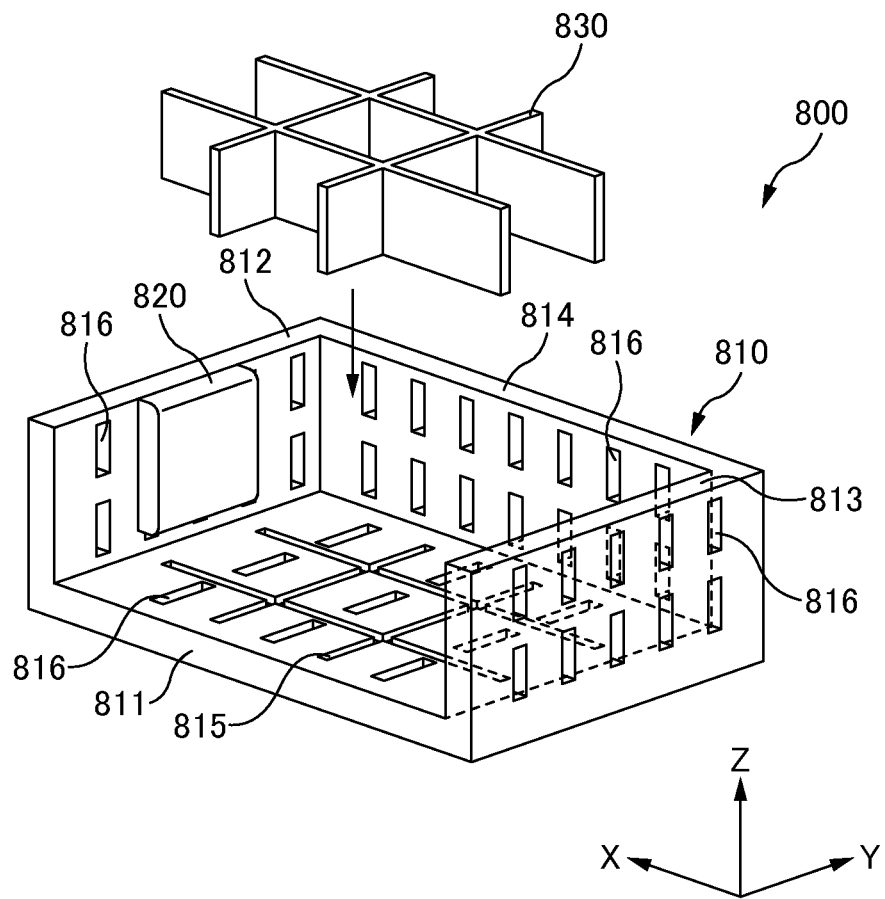
FIG. 12 is an exploded perspective view illustrating another example (seventh example) of a pharmaceutical storage box according to an embodiment of the present disclosure.
Figure 13:
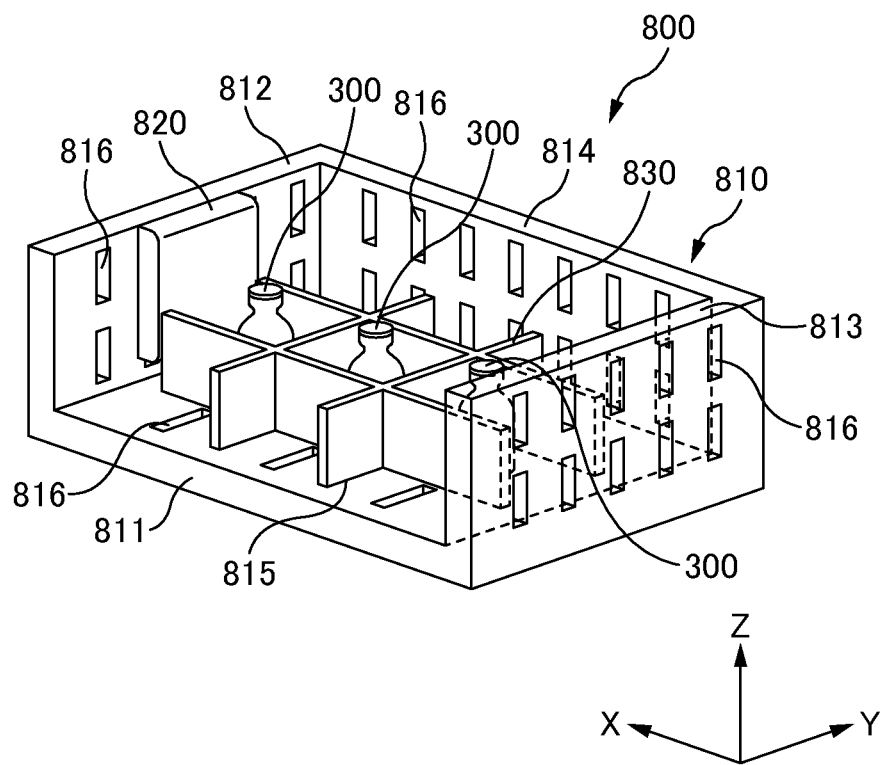
FIG. 13 is a perspective view illustrating a pharmaceutical storage box illustrated in FIG. 12.

FIG. 12 is an exploded perspective view illustrating another example of the pharmaceutical storage box according to an embodiment of the present disclosure. FIG. 13 is a perspective view illustrating the pharmaceutical storage box illustrated in FIG. 12. In FIGS. 12 and 13, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 800 is a box for storing the pharmaceuticals 300 to be managed.

The pharmaceutical storage box 800 includes a storage portion 810, an antenna 820, and a partition plate 830.

The storage portion 810 is defined by a total of four flat plates of a bottom plate 811, side plates 812, 813, and a back plate 814. The surface of the bottom plate 811 on which the pharmaceuticals 300 are to be placed has a groove 815 for stably arranging the partition plate 830.

The storage portion 810 may be formed, for example, such that the bottom plate 811, the side plates 812, 813, and the back plate 814 are integrally formed by die molding using a resin material. Alternatively, the storage portion 810 may be formed, for example, such that the bottom plate 811, the side plates 812, 813, and the back plate 814 are separately formed by die molding using a resin material, and then the bottom plate 811, the side plates 812, 813, and the back plate 814 are bonded to one another and/or adhesive or the like. The storage portion 810 has multiple air passage holes 816 in each of the bottom plate 811, the side plates 812, 813, and the back plate 814 such that the pharmaceuticals 300 stored in the storage portion 810 are effectively refrigerated by the air circulating in the inner case 120.

The antenna 820 is a device configured to transmit a radio wave in the storage portion 810 to activate the IC chip in the IC tag 310 attached to each pharmaceutical 300, and receive the ID information indicating the pharmaceutical 300. The ID information received by the antenna 820 is managed, by the controller described later, in association with the information on the refrigeration temperature and the put-in and take-out time points of the pharmaceutical 300.

The antenna 820 having a flat plate shape is attached to, for example, a surface of the side plate 812 facing the side plate 813.

When multiple pharmaceuticals 300 are stored in the pharmaceutical storage box 800 and the IC tags 310 overlap each other at a short distance, radio wave interference may occur between/among the loop coils of the IC tags 310, and thus the antenna 820 may not correctly receive the pieces of ID information indicating the respective pharmaceuticals 300 from the IC chips in the IC tags 310 thereof.

In this case, if the minimum distance between IC tags 310 adjacent to each other is equal to or greater than a certain distance, the antenna 820 can correctly receive the pieces of ID information indicating the respective pharmaceuticals 300 from the IC chips in the IC tags 310 thereof.

The partition plate 830 separates the pharmaceuticals 300 from one another by partitioning the storage portion 810 into sections such that the minimum distance between IC tags 310 adjacent to each other is equal to or greater than the certain distance. The partition plate 830 is formed, for example, by die molding using a resin material. The partition plate 830 is formed such that one or more flat plates parallel to the side plates 812, 813 are combined with one or more flat plates parallel to the back plate 814. In an embodiment of the present disclosure, the partition plate 830 is formed such that two flat plates parallel to the side plates 812, 813 are combined with two flat plates parallel to the back plate 814. A groove 815 in which the bottom surface of the partition plate 830 is to be fitted is formed on the surface of the bottom plate 811 on which the pharmaceuticals 300 are to be placed such that the partition plate 830 is stably arranged on the bottom plate 811.

Arranging the partition plate 830 on the bottom plate 811 maintains the minimum distance between IC tags 310 adjacent to each other at the certain distance or greater even when multiple pharmaceuticals 300 are stored in the pharmaceutical storage box 800. Accordingly, the antenna 820 can correctly receive the pieces of ID information indicating the respective pharmaceuticals 300 from the IC chips in the IC tags 310 thereof.

Eighth Example

Figure 14:
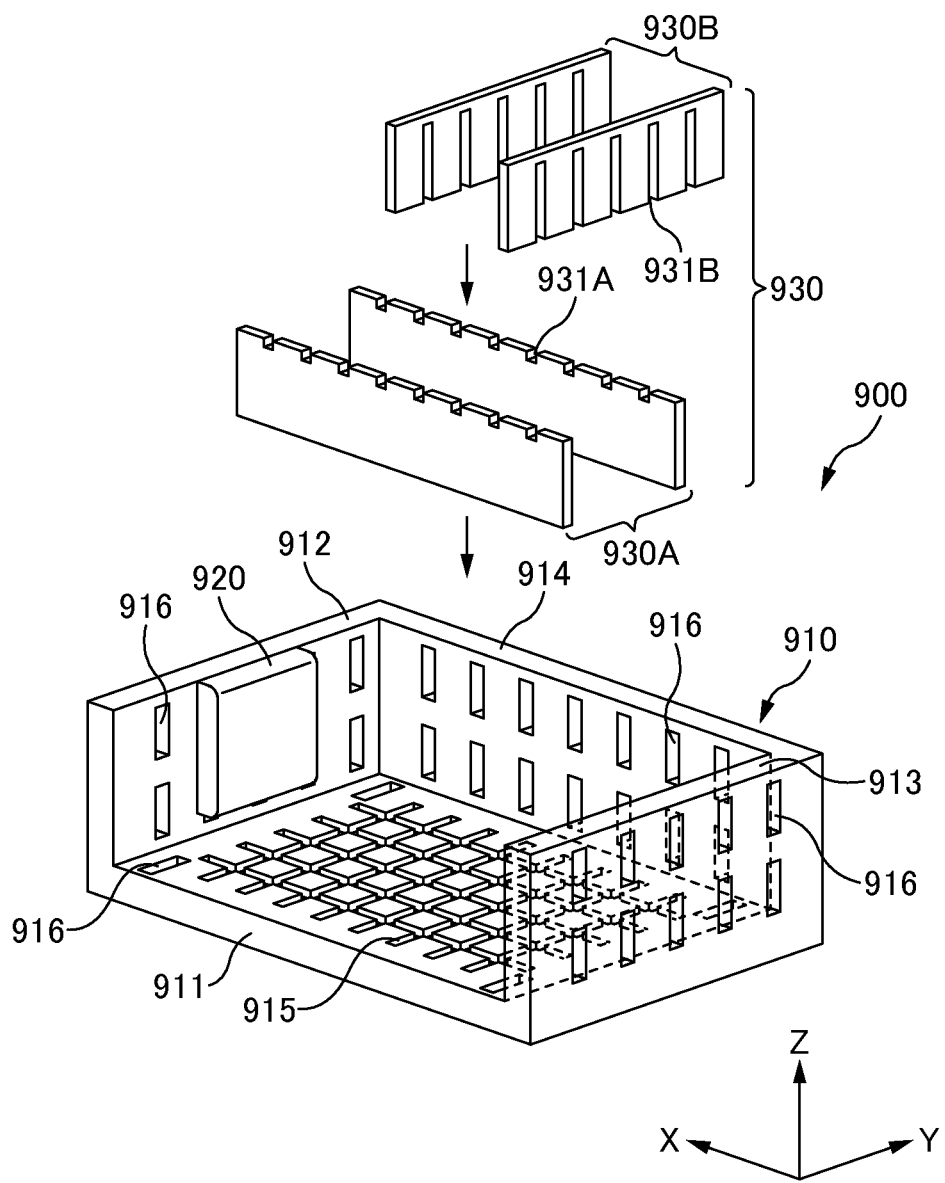
FIG. 14 is an exploded perspective view illustrating another example (eighth example) of a pharmaceutical storage box according to an embodiment of the present disclosure.
Figure 15:
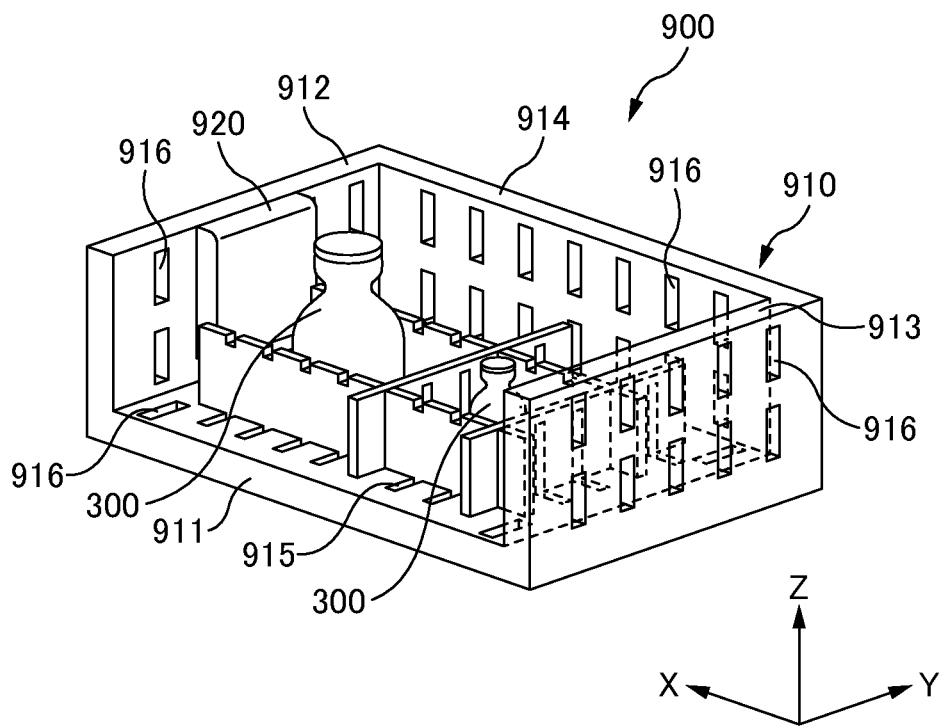
FIG. 15 is a perspective view illustrating a pharmaceutical storage box illustrated in FIG. 14.

FIG. 14 is an exploded perspective view illustrating another example of the pharmaceutical storage box according to an embodiment of the present disclosure. FIG. 15 is a perspective view illustrating the pharmaceutical storage box illustrated in FIG. 14. In FIGS. 14 and 15, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 900 is a box for storing the pharmaceuticals 300 to be managed.

The pharmaceutical storage box 900 includes a storage portion 910, an antenna 920, and a partition plate 930.

The storage portion 910 is defined by a total of four flat plates of a bottom plate 911, side plates 912, 913, and a back plate 914. The surface of the bottom plate 911 on which the pharmaceuticals 300 are to be placed has a groove 915 for stably arranging the partition plate 930.

The storage portion 910 may be formed, for example, such that the bottom plate 911, the side plates 912, 913, and the back plate 914 are integrally formed by die molding using a resin material. Alternatively, the storage portion 910 may be formed, for example, such that the bottom plate 911, the side plates 912, 913, and the back plate 914 are separately formed by die molding using a resin material, and then the bottom plate 911, the side plates 912, 913, and the back plate 914 are bonded to one another and/or adhesive or the like. The storage portion 910 has multiple air passage holes 916 in each of the bottom plate 911, the side plates 912, 913, and the back plate 914 such that the pharmaceuticals 300 stored in the storage portion 910 are effectively refrigerated by the air circulating in the inner case 120.

The antenna 920 is a device configured to transmit a radio wave in the storage portion 910 to activate the IC chip in the IC tag 310 attached to each pharmaceutical 300, and receive the ID information indicating the pharmaceutical 300. The ID information received by the antenna 920 is managed, by the controller described later, in association with the information on the refrigeration temperature and the put-in and take-out time points of the pharmaceutical 300.

The antenna 920 having a flat plate shape is attached to, for example, a surface of the side plate 912 facing the side plate 913.

In the seventh example, the sections separated from one another by the partition plate 830 each have a predetermined shape. Accordingly, pharmaceuticals 300 having various sizes may not be stored.

The partition plate 930 partitions the storage portion 910 into sections to separate the pharmaceuticals 300 from one another such that the minimum distance between IC tags 310 adjacent to each other is equal to or greater than the certain distance, and has such a structure that the sizes of the respective sections can be changed according to the sizes of the pharmaceuticals 300 to be stored therein. The partition plate 930 is formed such that one or more flat plates 930B parallel to the side plates 912, 913 are combined with one or more flat plates 930A parallel to the back plate 914. In an embodiment of the present application, the partition plate 930 is formed such that two flat plates parallel to the side plates 912, 913 are combined with two flat plates parallel to the back plate 914. The flat plates 930A have strip-shaped recesses 931A on a surface (+Z side surface) not facing the bottom plate 911, the recesses 931A being arranged in the longitudinal direction of this surface. In addition, the flat plates 930B have strip-shaped recesses 931B on a surface (−Z side surface) facing the bottom plate 911, the recesses 931B arranged in the longitudinal direction of this surface. Then, the recess 931B at a predetermined position in the flat plate 930B is inserted into the recess 931A at a predetermined position in the flat plate 930A according to the sizes of the pharmaceuticals 300 to be stored, thereby being able to form the partition plate 930 having sections of various sizes. The partition plate 930 may be formed, for example, by die molding using a resin material. A groove 915, in which the bottom surface of the partition plate 930 is to be fitted, is formed on the surface of the bottom plate 911 on which the pharmaceuticals 300 are to be placed such that the partition plate 930 is stably arranged on the bottom plate 911.

Arranging the partition plate 930 on the bottom plate 911 maintains the minimum distance between IC tags 310 adjacent to each other at the certain distance or greater even when multiple pharmaceuticals 300 of various sizes are stored in the pharmaceutical storage box 900. Accordingly, the antenna 920 can correctly receive the pieces of ID information indicating the respective pharmaceuticals 300 from the IC chips in the IC tags 310 thereof.

Ninth Example

Figure 16:
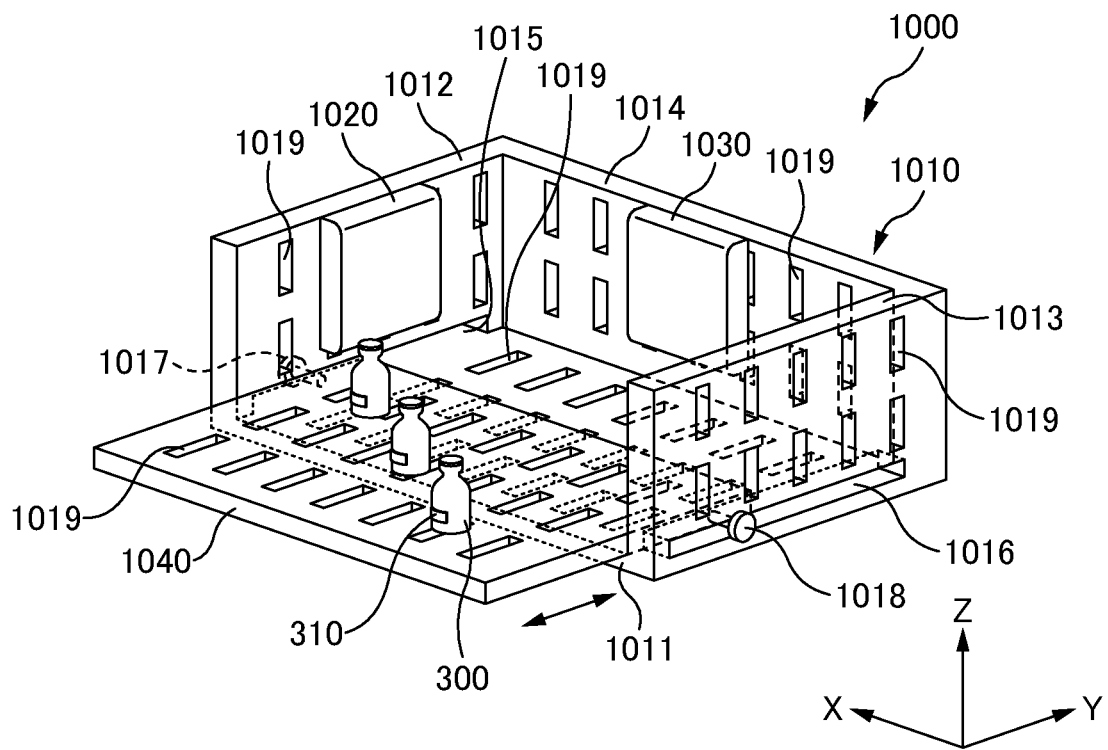
FIG. 16 is a perspective view illustrating another example (ninth example) of a pharmaceutical storage box according to an embodiment of the present disclosure.

FIG. 16 is a perspective view illustrating another example of the pharmaceutical storage box according to an embodiment of the present disclosure. In FIG. 16, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 1000 is a box for storing the pharmaceuticals 300 to be managed.

The pharmaceutical storage box 1000 includes a storage portion 1010, antennas 1020, 1030, and a tray 1040.

The storage portion 1010 is defined by a total of four flat plates of a bottom plate 1011, side plates 1012, 1013, and a back plate 1014. The side plate 1012 has a long hole 1015 for moving the tray 1040 in and out of the storage portion 1010, the long hole 1015 extending in a longitudinal direction (direction of the Y-axis) of the side plate 1012. Similarly, the side plate 1013 has a long hole 1016 for moving the tray 1040 in and out of the storage portion 1010, the long hole 1016 extending in a longitudinal direction (direction of the Y-axis) of the side plate 1013.

The storage portion 1010 may be formed, for example, such that the bottom plate 1011, the side plates 1012, 1013, and the back plate 1014 are integrally formed by die molding using a resin material. Alternatively, the storage portion 1010 may be formed, for example, such that the bottom plate 1011, the side plates 1012, 1013, and the back plate 1014 are separately formed by die molding using a resin material, and then the bottom plate 1011, the side plates 1012, 1013, and the back plate 1014 are bonded to one another with adhesive or the like.

The tray 1040 is a horizontal plate on which the pharmaceuticals 300 are to be placed. The tray 1040 is attached to the storage portion 1010 so as to be movable on the bottom plate 1011 in the longitudinal directions (directions of the Y-axis) of the side plates 1012, 1013. Specifically, one of side surfaces (+X side surface extending along a plane formed by the Y-axis and the Z-axis) of the tray 1040 is coupled to a roller 1017 through the long hole 1015, and the other side surface (−X side surface extending along a plane formed by the Y-axis and the Z-axis) of the tray 1040 is coupled to a roller 1018 through the long hole 1016. The rollers 1017, 1018 are guided by the long holes 1015, 1016, respectively, such that the tray 1040 can be moved in and out of the storage portion 1010.

The storage portion 1010 has multiple air passage holes 1019 in each of the bottom plate 1011, the side plates 1012, 1013, and the back plate 1014 such that the pharmaceuticals 300 stored in the storage portion 1010 are effectively refrigerated by the air circulating in the inner case 120. In addition, the tray 1040 also has multiple air passage holes 1019.

The antennas 1020, 1030 are devices configured to transmit radio waves in the storage portion 1010 to activate the IC chip in the IC tag 310 attached to each pharmaceutical 300, and receive the ID information indicating the pharmaceutical 300. The ID information received by the antennas 1020, 1030 is managed by the controller described later in association with the information on the refrigeration temperature and the put-in and take-out time points of the pharmaceutical 300.

The antenna 1020 having a flat plate shape is attached to, for example, a surface of the side plate 1012 facing the side plate 1013. The antenna 1030 having a flat plate shape is attached to a surface of the back plate 1014 between the side plates 1012 and 1013. The surface (surface extending along a plane formed by the Y-axis and the Z-axis) of the antenna 1020 is thus perpendicular to the surface (surface extending along a plane formed by the X-axis and the Z-axis) of the antenna 1030.

The tray 1040 can be moved in and out of the storage portion 1010 while the storage portion 1010 is stored in the inner case 120. This produces another effect of facilitating work of putting in or taking out the pharmaceuticals 300 in addition to the effects of the second example.

Tenth Example

Figure 17:
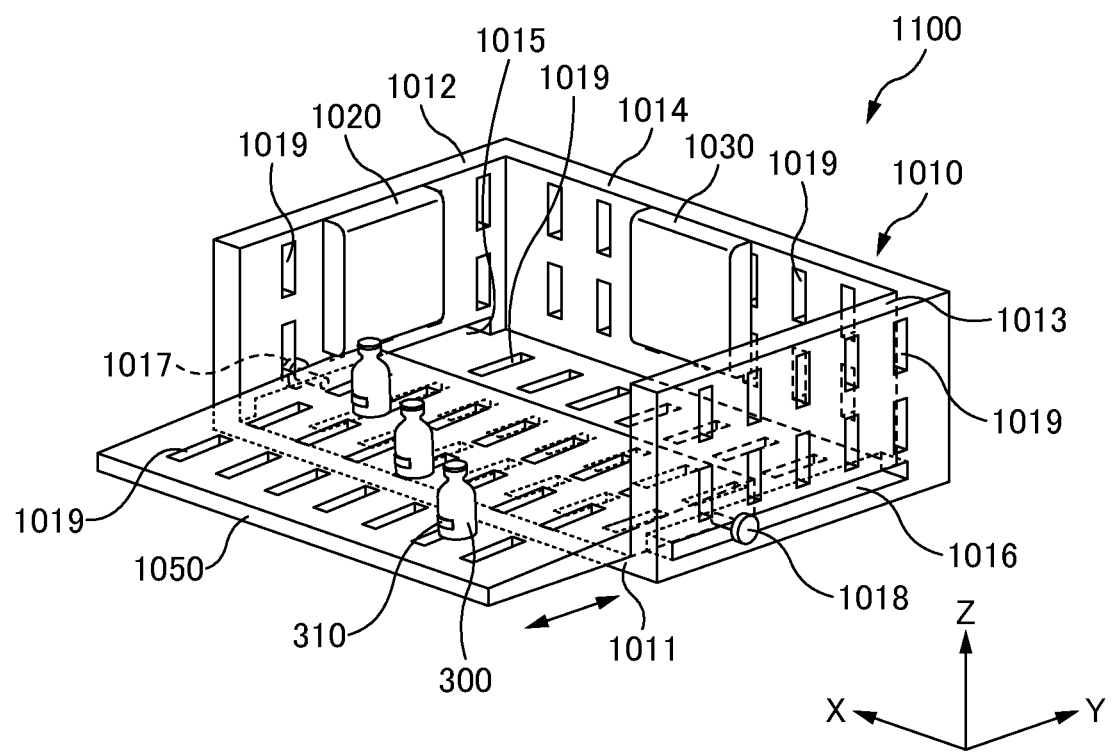
FIG. 17 is a perspective view illustrating another example (tenth example) of a pharmaceutical storage box according to an embodiment of the present disclosure.

FIG. 17 is a perspective view illustrating another example of the pharmaceutical storage box according to an embodiment of the present disclosure. In FIG. 17, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box. Note that, in the tenth example, the same components as those in the ninth example are denoted by the same reference numerals and description thereof is omitted.

A pharmaceutical storage box 1100 is a box for storing the pharmaceuticals 300 to be managed.

The pharmaceutical storage box 1100 includes the storage portion 1010, the antennas 1020, 1030, and a tray 1050.

The tray 1050 is a tilted plate on which the pharmaceuticals 300 are to be placed. Specifically, a surface (+Z side surface) of the tray 1050 on which the pharmaceuticals 300 are to be placed is tilted downward (toward the −Z direction) as it extends away from the back plate 1014 (toward the −Y direction). The tray 1050 is attached to the storage portion 1010 so as to be movable on the bottom plate 1011 in the longitudinal directions (directions of the Y-axis) of the side plates 1012, 1013. Specifically, one of side surfaces (+X side surface extending along a plane formed by the Y-axis and the Z-axis) of the tray 1050 is coupled to the roller 1017 through the long hole 1015, and the other side surface (−X side surface extending along a plane formed by the Y-axis and the Z-axis) of the tray 1050 is coupled to the roller 1018 through the long hole 1016. The rollers 1017, 1018 are guided by the long holes 1015, 1016, respectively, such that the tray 1050 can be moved in and out of the storage portion 1010.

As in the storage portion 1010, the tray 1050 has multiple air passage holes 1019 such that the pharmaceuticals 300 stored in the storage portion 1010 are effectively refrigerated by the air circulating in the inner case 120.

The tray 1050 can be moved in and out of the storage portion 1010 while the storage portion 1010 is stored in the inner case 120. This produces another effect of facilitating work of putting in or taking out the pharmaceuticals 300 in addition to the effects of the fifth example.

The surface of the tray 1050 on which the pharmaceuticals 300 are to be placed may be tilted downward (toward the −Z direction) as it extends away from the side plate 1012 (toward the −X direction) or tilted downward (toward the −Z direction) as it extends away from the side plate 1013 (toward the +X direction), instead of being tilted downward (toward the −Z direction) as it extends away from the back plate 1014 (toward the −Y direction).

Eleventh Example

Figure 18:
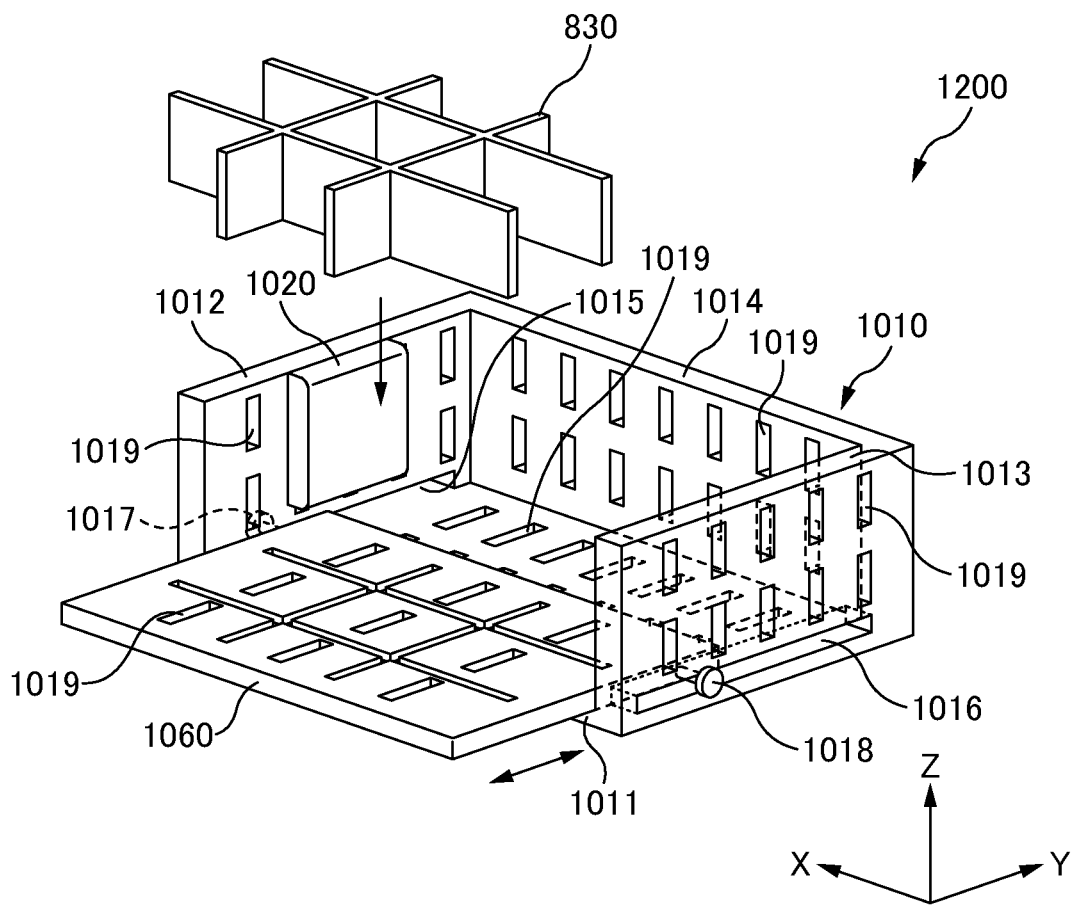
FIG. 18 is an exploded perspective view illustrating another example (eleventh example) of a pharmaceutical storage box according to an embodiment of the present disclosure.
Figure 19:
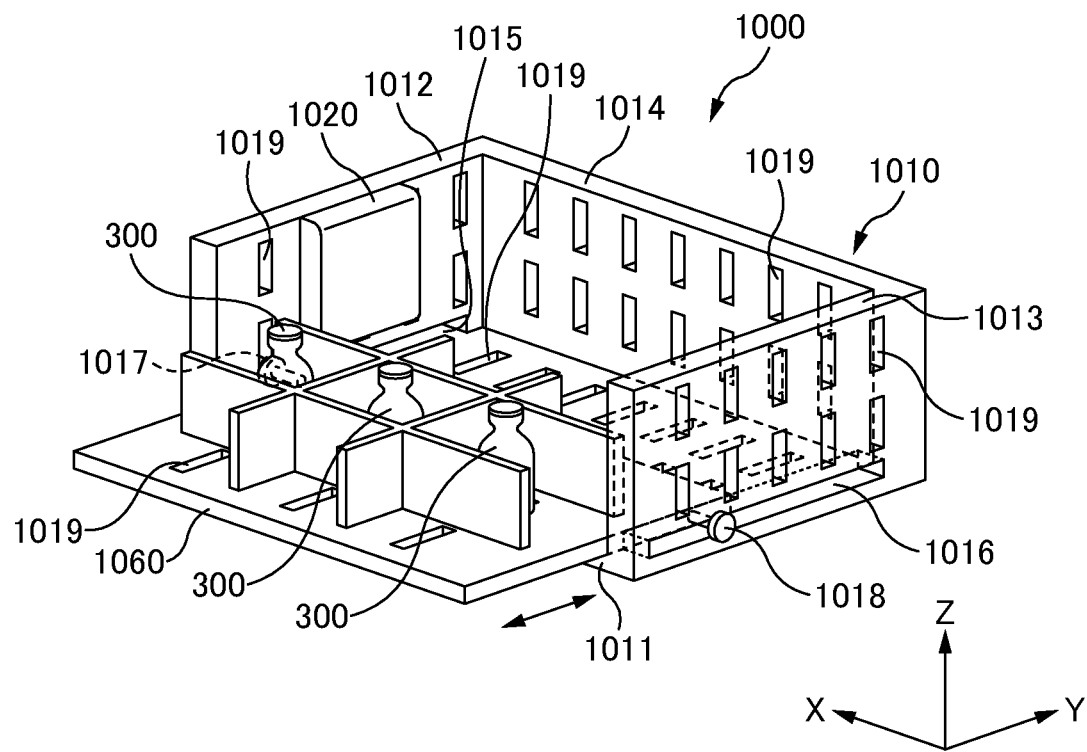
FIG. 19 is a perspective view illustrating a pharmaceutical storage box illustrated in FIG. 18.

FIG. 18 is an exploded perspective view illustrating another example of the pharmaceutical storage box according to an embodiment of the present disclosure. FIG. 19 is a perspective view illustrating the pharmaceutical storage box illustrated in FIG. 18. In FIGS. 18 and 19, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box. Note that, in the eleventh example, the same components as those in the seventh and ninth examples are denoted by the same reference numerals and description thereof is omitted.

A pharmaceutical storage box 1200 is a box for storing the pharmaceuticals 300 to be managed.

The pharmaceutical storage box 1200 includes the storage portion 1010, the antenna 1020, a tray 1060, and the partition plate 830.

The tray 1060 is a horizontal plate on which the pharmaceuticals 300 are to be placed. The surface of the tray 1060 on which the pharmaceuticals 300 are to be placed has a groove 1061 for stably arranging the partition plate 830. The tray 1060 is attached to the storage portion 1010 so as to be movable on the bottom plate 1011 in the longitudinal directions (directions of the Y-axis) of the side plates 1012, 1013. Specifically, one of side surfaces (+X side surface extending along a plane formed by the Y-axis and the Z-axis) of the tray 1060 is coupled to the roller 1017 through the long hole 1015, and the other side surface (−X side surface extending along a plane formed by the Y-axis and the Z-axis) of the tray 1060 is coupled to the roller 1018 through the long hole 1016. The rollers 1017, 1018 are guided by the long holes 1015, 1016, respectively, such that the tray 1060 can be moved in and out of the storage portion 1010.

As in the storage portion 1010, the tray 1060 has multiple air passage holes 1019 such that the pharmaceuticals 300 stored in the storage portion 1010 are effectively refrigerated by the air circulating in the inner case 120.

The tray 1060 can be moved in and out of the storage portion 1010 while the storage portion 1010 is stored in the inner case 120. This produces another effect of facilitating work of putting in or taking out the pharmaceuticals 300 in addition to the effects of the seventh example.

Twelfth Example

Figure 20:
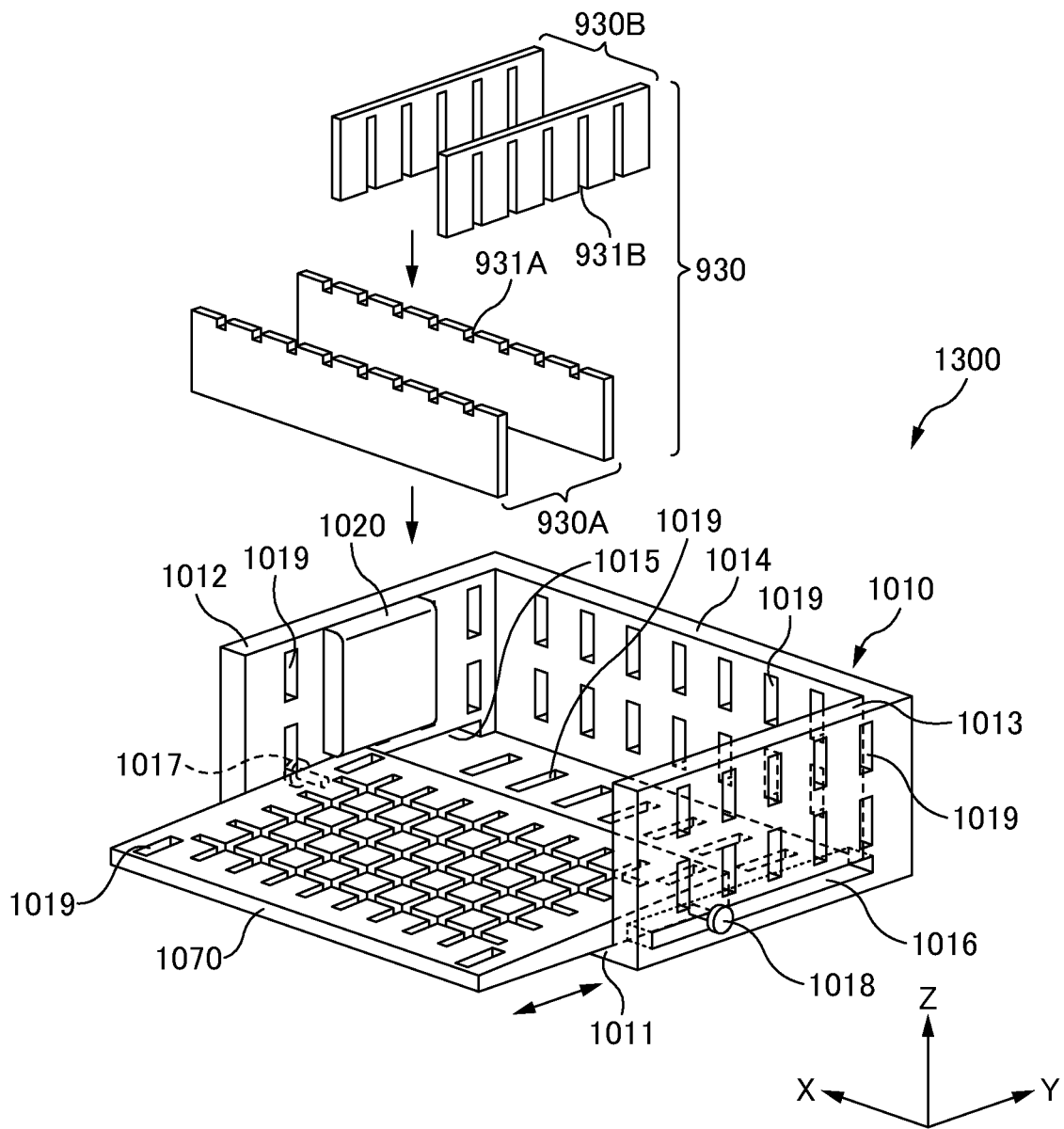
FIG. 20 is an exploded perspective view illustrating another example (twelfth example) of a pharmaceutical storage box according to an embodiment of the present disclosure.
Figure 21:
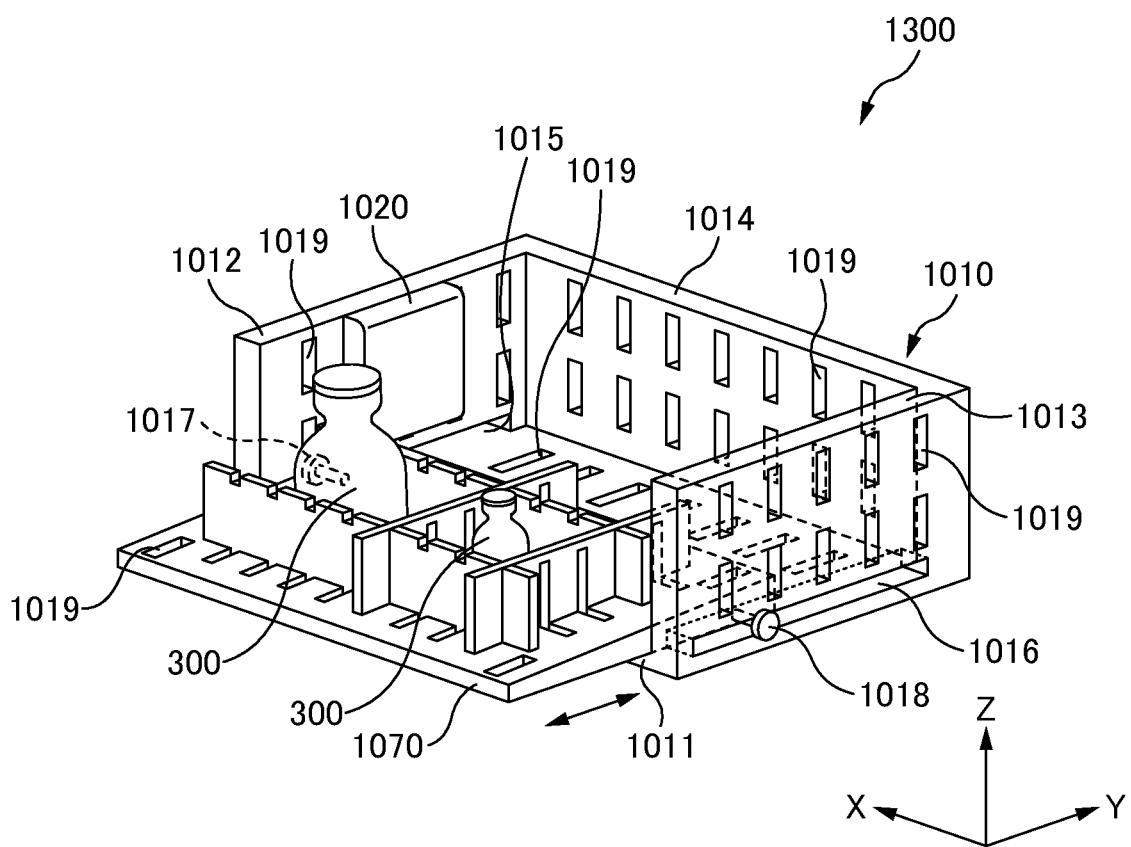
FIG. 21 is a perspective view illustrating a pharmaceutical storage box illustrated in FIG. 20.

FIG. 20 is an exploded perspective view illustrating another example of the pharmaceutical storage box according to an embodiment of the present disclosure. FIG. 21 is a perspective view illustrating the pharmaceutical storage box illustrated in FIG. 20. In FIGS. 20 and 21, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box. Note that, in the twelfth example, the same components as those in the eighth and ninth examples are denoted by the same reference numerals and description thereof is omitted.

A pharmaceutical storage box 1300 is a box for storing the pharmaceuticals 300 to be managed.

The pharmaceutical storage box 1300 includes the storage portion 1010, the antenna 1020, a tray 1070, and the partition plate 930.

The tray 1070 is a horizontal plate on which the pharmaceuticals 300 are to be placed. The surface of the tray 1070 on which the pharmaceuticals 300 are to be placed has a groove 1071 for stably arranging the partition plate 930.

The tray 1070 is attached to the storage portion 1010 so as to be movable on the bottom plate 1011 in the longitudinal directions (directions of the Y-axis) of the side plates 1012, 1013. Specifically, one of side surfaces (+X side surface extending along a plane formed by the Y-axis and the Z-axis) of the tray 1070 is coupled to the roller 1017 through the long hole 1015 and the other side surface (−X side surface extending along a plane formed by the Y-axis and the Z-axis) of the tray 1070 is coupled to the roller 1018 through the long hole 1016. The rollers 1017, 1018 are guided by the long holes 1015, 1016, respectively, such that the tray 1070 can be moved in and out of the storage portion 1010.

As in the storage portion 1010, the tray 1070 has multiple air passage holes 1019 such that the pharmaceuticals 300 stored in the storage portion 1010 are effectively refrigerated by the air circulating in the inner case 120.

The tray 1070 can be moved in and out of the storage portion 1010 while the storage portion 1010 is stored in the inner case 120. This produces another effect of facilitating work of putting in or taking out the pharmaceuticals 300 in addition to the effects of the eighth example.

Thirteenth Example

Figure 23:
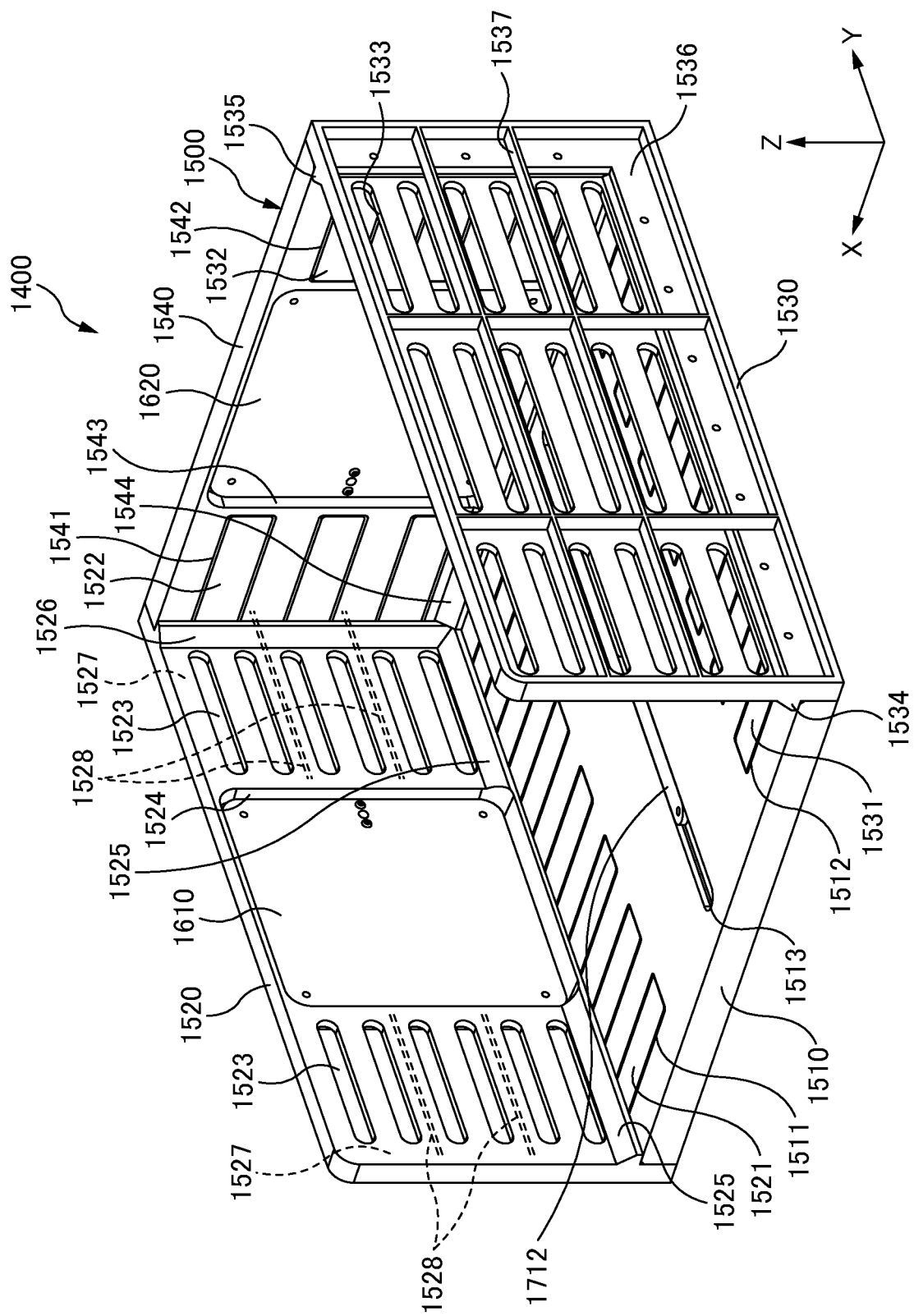
FIG. 23 is a perspective view illustrating one example of a pharmaceutical storage box according to an embodiment of the present disclosure in a state in which the width of a pharmaceutical storage box is reduced.
Figure 24:
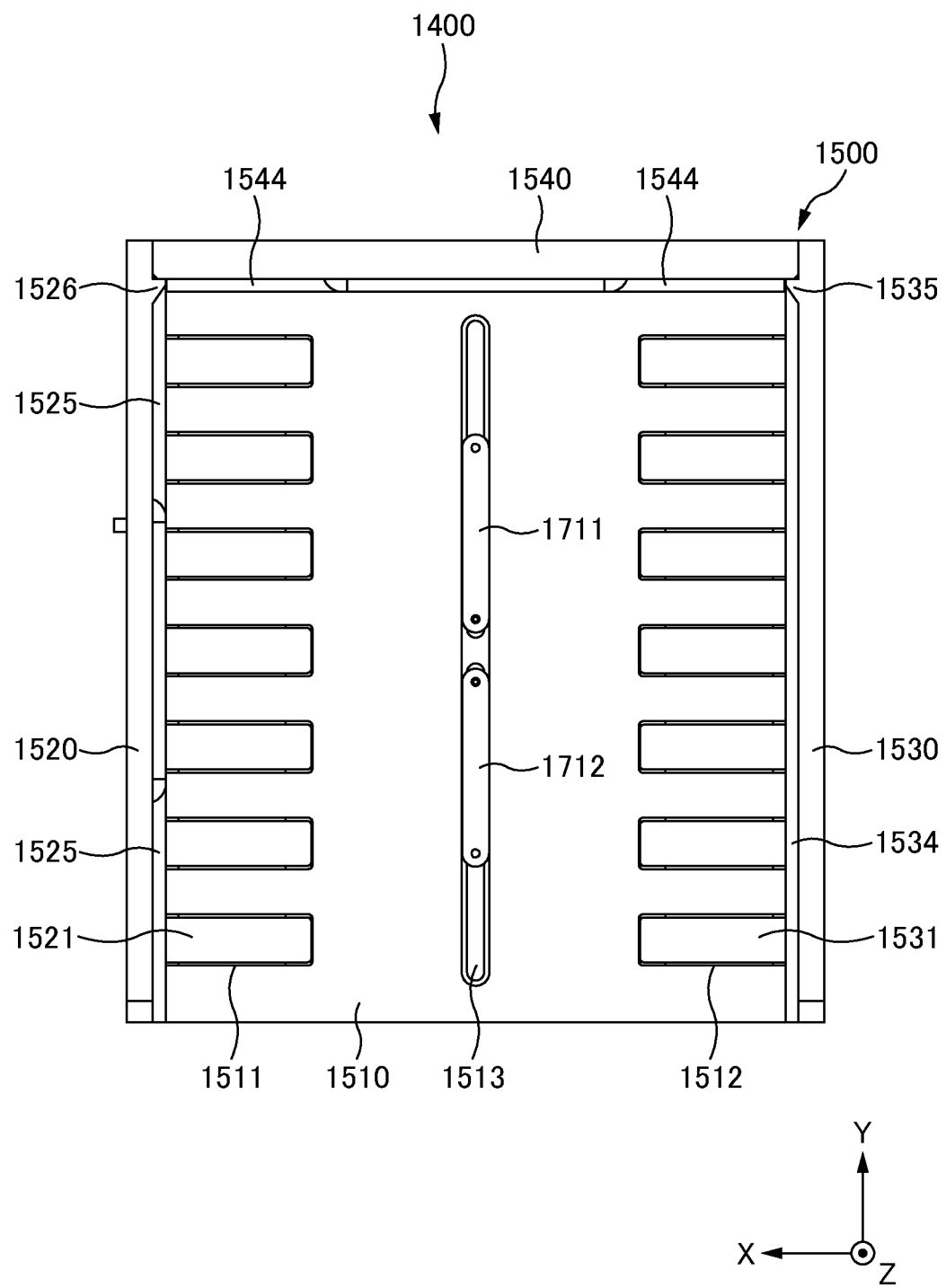
FIG. 24 is a plan view illustrating a pharmaceutical storage box of FIG. 23 when viewed from an upper surface toward a bottom plate.
Figure 25:
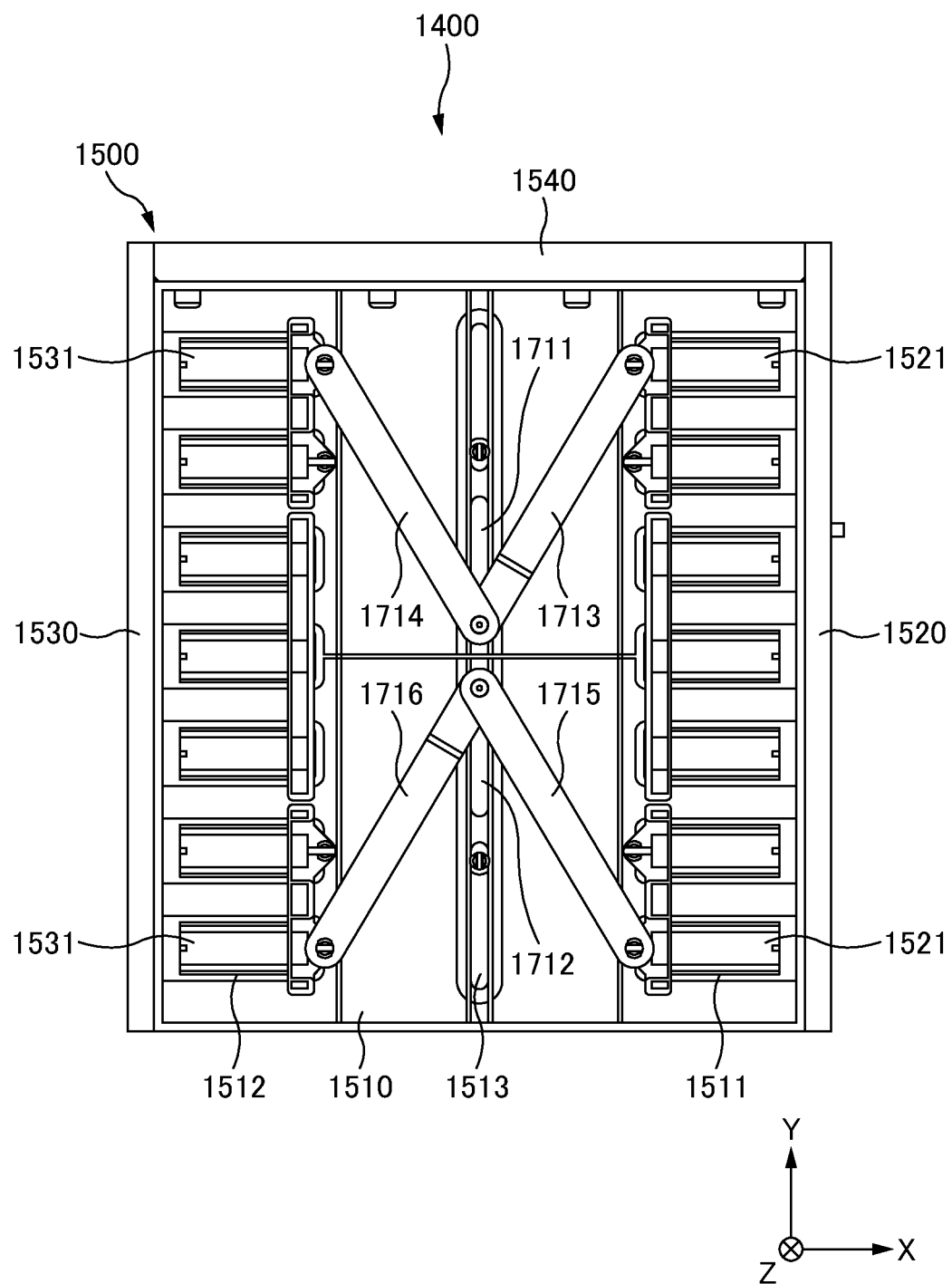
FIG. 25 is a plan view illustrating a pharmaceutical storage box of FIG. 23 when viewed from below a bottom plate toward an upper surface.
Figure 26:
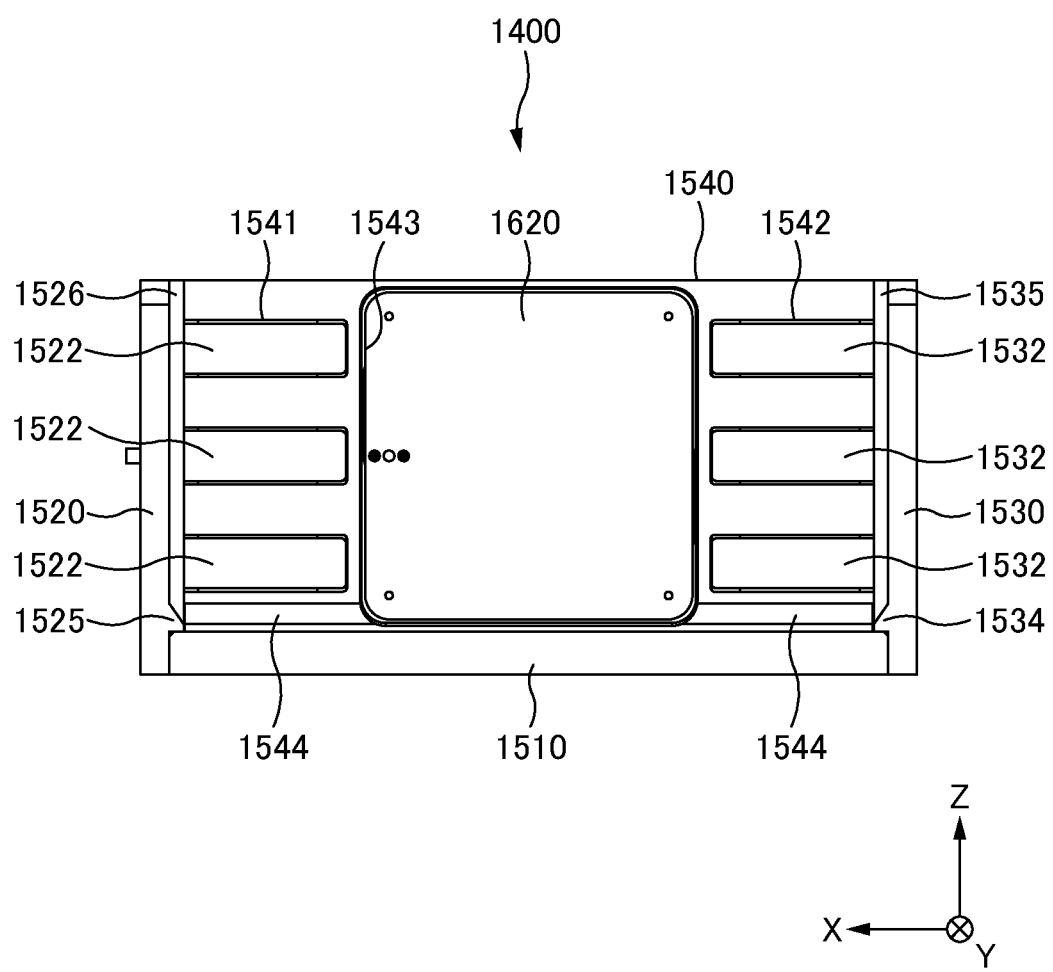
FIG. 26 is a plan view illustrating a pharmaceutical storage box of FIG. 23 when viewed from a front surface toward a back surface.

FIG. 23 is a perspective view illustrating one example of the pharmaceutical storage box according to an embodiment of the present disclosure in a state in which the width of the pharmaceutical storage box is reduced. FIG. 24 is a plan view illustrating the pharmaceutical storage box of FIG. 23 when viewed from an upper surface toward a bottom plate. FIG. 25 is a plan view illustrating the pharmaceutical storage box of FIG. 23 when viewed from below the bottom plate toward the upper surface. FIG. 26 is a plan view illustrating the pharmaceutical storage box of FIG. 23 when viewed from a front surface toward a back surface.

Figure 27:
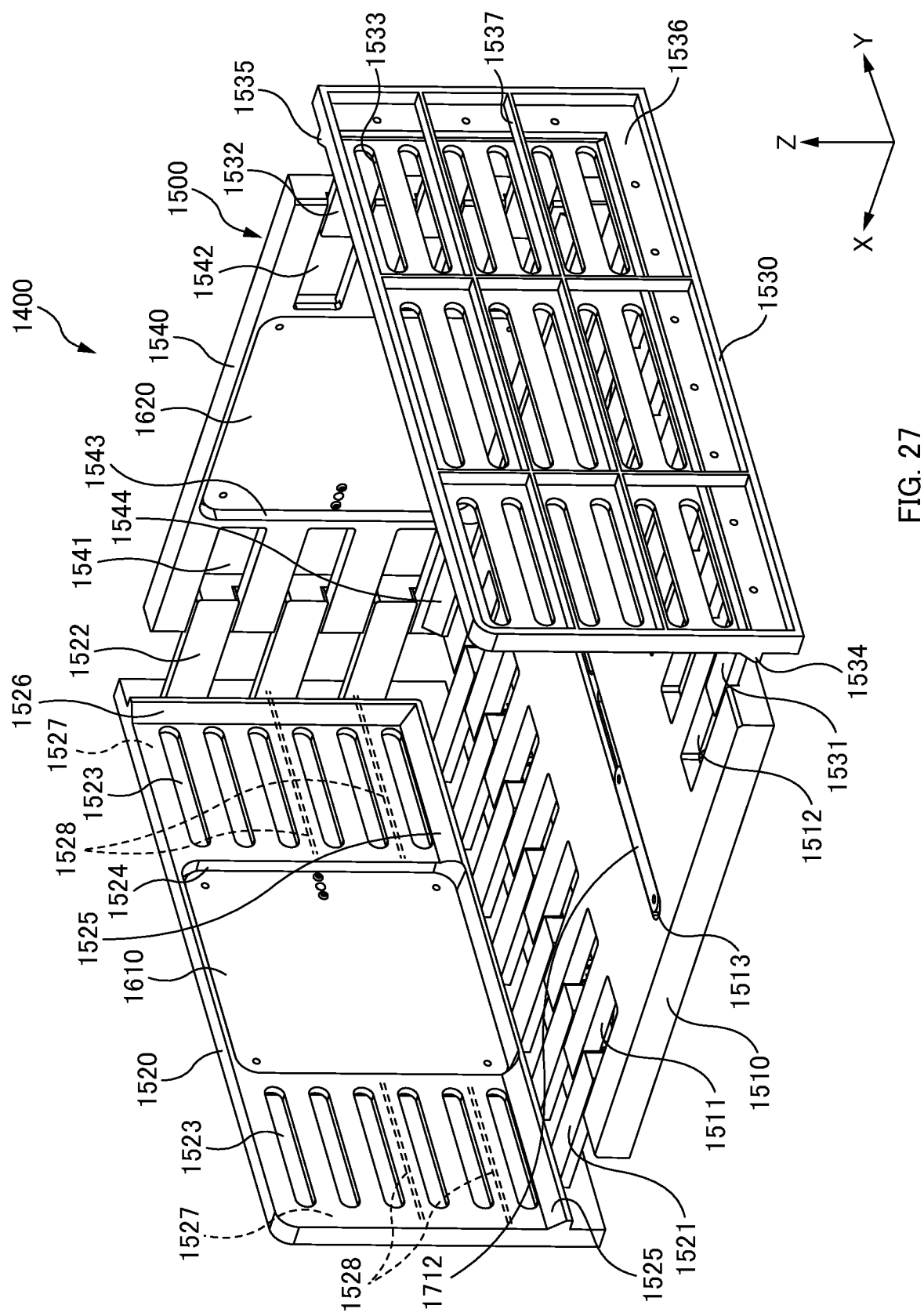
FIG. 27 is a perspective view illustrating one example of a pharmaceutical storage box according to an embodiment of the present disclosure in a state in which the width of a pharmaceutical storage box is increased.
Figure 28:
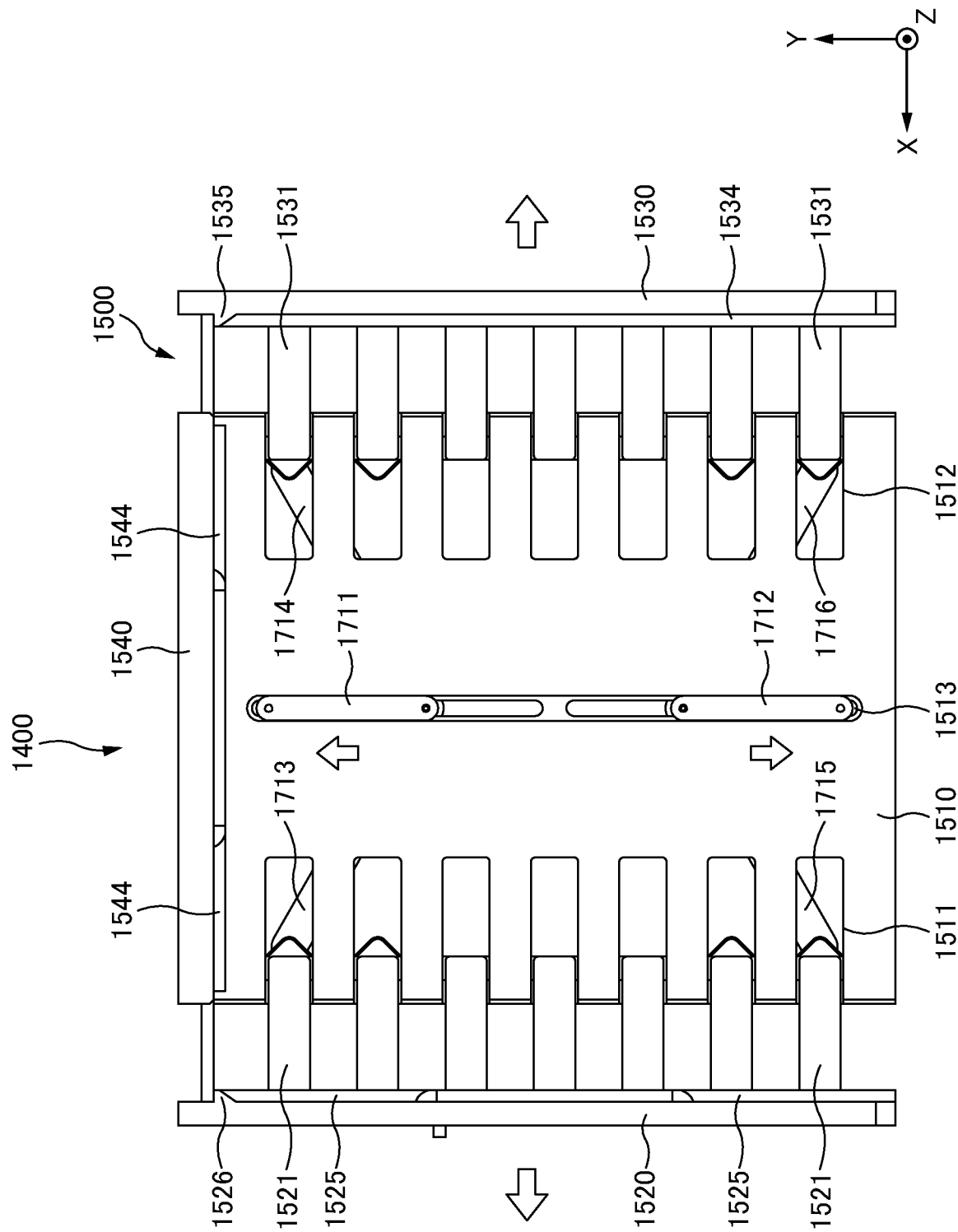
FIG. 28 is a plan view illustrating a pharmaceutical storage box of FIG. 27 when viewed from an upper surface toward a bottom plate.
Figure 29:
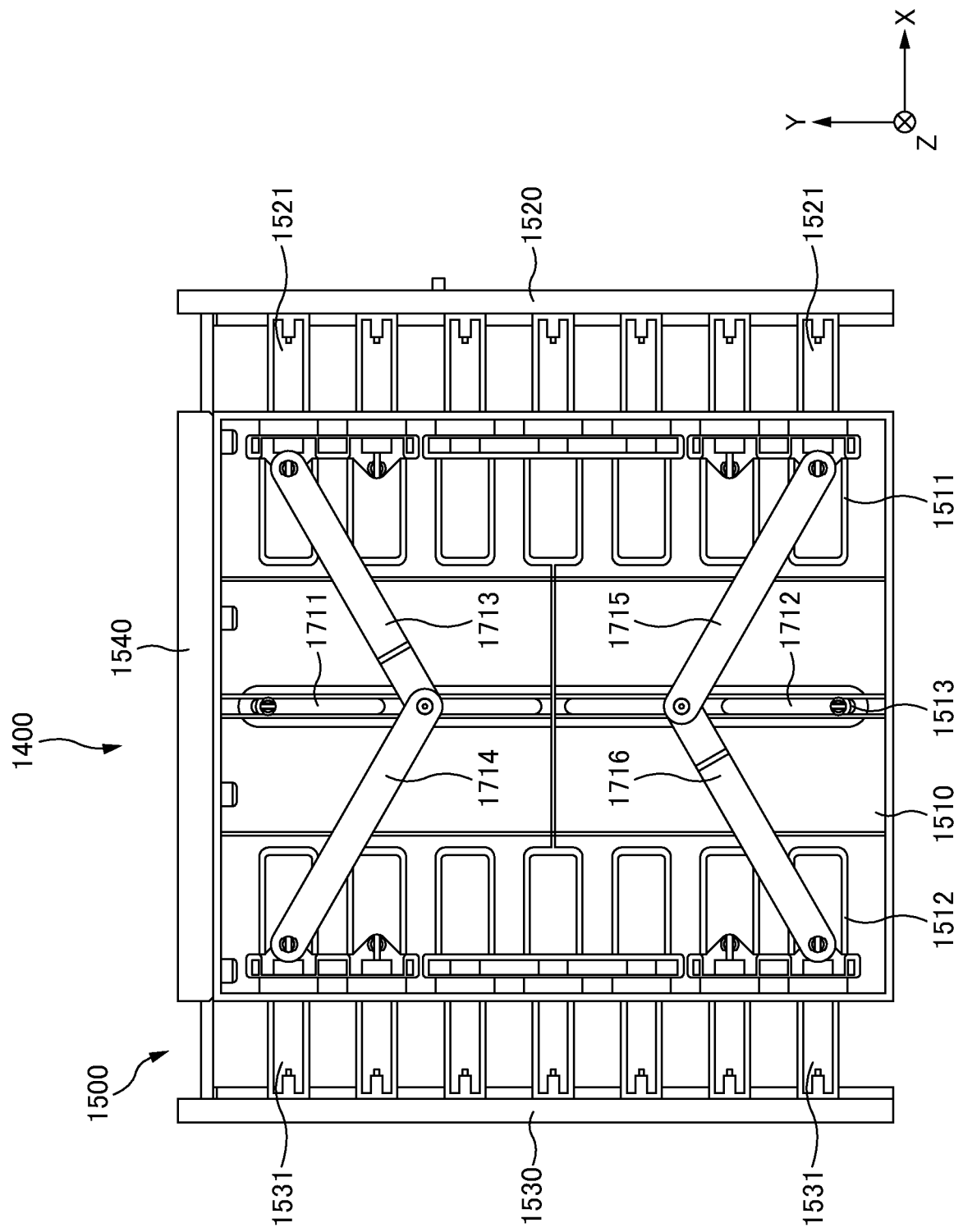
FIG. 29 is a plan view illustrating a pharmaceutical storage box of FIG. 27 when viewed from below a bottom plate toward an upper surface.
Figure 30:
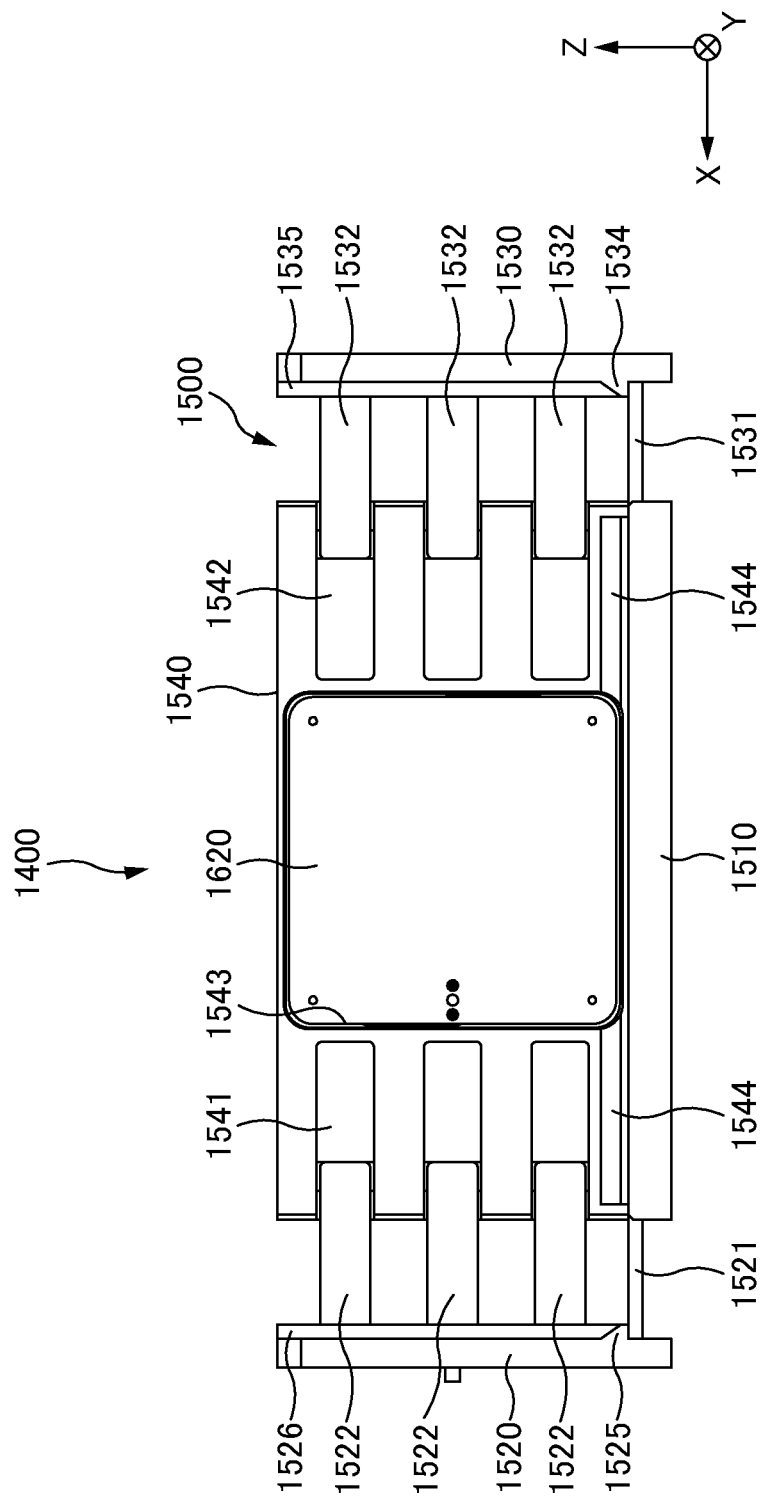
FIG. 30 is a plan view illustrating a pharmaceutical storage box of FIG. 27 when viewed from a front surface toward a back surface.

Meanwhile, FIG. 27 is a perspective view illustrating the one example of the pharmaceutical storage box according to an embodiment of the present disclosure in a state in which the width of the pharmaceutical storage box is increased. FIG. 28 is a plan view illustrating the pharmaceutical storage box of FIG. 27 when viewed from the upper surface toward the bottom plate. FIG. 29 is a plan view illustrating the pharmaceutical storage box of FIG. 27 when viewed from below the bottom plate toward the upper surface. FIG. 30 is a plan view illustrating the pharmaceutical storage box of FIG. 27 when viewed from the front surface toward the back surface.

In FIGS. 23 to 30, an X-axis is an axis extending in a width direction of the pharmaceutical storage box, a Y-axis is an axis extending in a front-back direction of the pharmaceutical storage box, and a Z-axis is an axis extending in a height direction of the pharmaceutical storage box.

A pharmaceutical storage box 1400 is a box for storing the pharmaceuticals 300 to be managed, and has such a configuration that the width (in a direction along the X-axis) thereof can be changed according to the volume of the inside of the inner case 120, the number of pharmaceutical storage boxes to be stored in the inner case 120, and/or the like.

The pharmaceutical storage box 1400 includes a storage portion 1500 and antennas 1610, 1620.

The storage portion 1500 is defined by a total of four flat plates of a bottom plate 1510, side plates 1520, 1530, and a back plate 1540. In the storage portion 1500, it is assumed that, for example, the bottom plate 1510, the side plates 1520, 1530, and the back plate 1540 are separately formed by die molding using a resin material, and then joined to one another such that the side plates 1520, 1530 are slidable with respect to the bottom plate 1510 and the back plate 1540 in the width directions (directions along the X-axis) of the storage portion 1500. Note that the bottom plate 1510 and the back plate 1540 may be integrally formed by die molding.

The bottom plate 1510 has multiple fitting grooves 1511, 1512 and a slide hole 1513.

The multiple fitting grooves 1511 are strip-shaped grooves for sliding the side plate 1520 in the width directions of the storage portion 1500, and are formed to be arranged along an end of the bottom plate 1510 on the side (+X side) on which the side plate 1520 is joined in a slidable manner. Meanwhile, the multiple fitting grooves 1512 are strip-shaped grooves for sliding the side plate 1530 in the width directions of the storage portion 1500, and are formed to be arranged along an end of the bottom plate 1510 on the side (−X side) on which the side plate 1530 is joined in a slidable manner.

The slide hole 1513 is a long hole for sliding two link pieces 1711, 1712 in the front-back directions (directions along the Y-axis) of the storage portion 1500 in association with the sliding of the side plates 1520, 1530 in the width directions of the storage portion 1500, and is formed, in an intermediate portion between the side plates 1520 and 1530, along the front-back direction (direction along the Y-axis) of the bottom plate 1510.

The back plate 1540 has multiple fitting grooves 1541, 1542, a recess 1543, and restriction ribs 1544 and is integrally joined to the bottom plate 1510.

The multiple fitting grooves 1541 are strip-shaped grooves for sliding the side plate 1520 in the width directions of the storage portion 1500, and are formed to be arranged along an end of the back plate 1540 on the side (+X side) on which the side plate 1520 is joined in a slidable manner. Meanwhile, the multiple fitting grooves 1542 are strip-shaped grooves for sliding the side plate 1530 in the width directions of the storage portion 1500, and are formed to be arranged along an end of the back plate 1540 on the side (−X side) on which the side plate 1530 is joined in a slidable manner.

The recess 1543 has a recessed shape in which the flat-plate-shaped antenna 1620 can be fitted, and is formed on a surface of the back plate 1540 on the bottom plate 1510 side (−Y side), between the multiple fitting grooves 1541 and 1542. The depth of the recess 1543 (length in the direction along the Y-axis) is designed to be greater than the thickness (length in the direction along the Y-axis) of the antenna 1620. Accordingly, the antenna 1620 is attached to the back plate 1540 such that an antenna surface of the antenna 1620 on the bottom plate 1510 side (−Y side) is recessed from a surface of the back plate 1540 on the bottom plate 1510 side (−Y side).

The restriction ribs 1544 are long pieces that restrict movement of the pharmaceuticals 300 toward the back plate 1540 (+Y side) to prevent the pharmaceuticals 300 from contacting the back plate 1540, and are integrally formed, at a right-angle corner portion between the bottom plate 1510 and the back plate 1540, along the width direction of the storage portion 1500. The shapes of the restriction ribs 1544 may be any shapes as long as the restriction ribs 1544 can restrict movement of the pharmaceuticals 300 toward the back plate 1540. For example, each of exposed surfaces of the restriction ribs 1544 may be a surface tilted toward the bottom plate 1510 as it extend away from the back plate 1540 or a step surface formed of two surfaces that are along the bottom plate 1510 and the back plate 1540, respectively.

The side plate 1520 has multiple fitting pieces 1521, 1522, multiple air passage holes 1523, recesses 1524, 1527, restriction ribs 1525, 1526, and reinforcement ribs 1528.

The multiple fitting pieces 1521 are strip-shaped pieces for sliding the side plate 1520 in the width directions of the storage portion 1500, and are formed to protrude from an end of the side plate 1520 on the bottom plate 1510 side (−Z side) toward the bottom plate 1510 so as to be fitted into the multiple fitting grooves 1511 of the bottom plate 1510. Similarly, the multiple fitting pieces 1522 are strip-shaped pieces for sliding the side plate 1520 in the width directions of the storage portion 1500, and are formed to protrude from an end of the side plate 1520 on the back plate 1540 side (+Y side) toward the back plate 1540 so as to be fitted into the multiple fitting grooves 1541 of the back plate 1540. Note that, for example, guide pieces and guide grooves may be provided on outer peripheral surfaces of the multiple fitting pieces 1521, 1522 and inner peripheral surfaces of the multiple fitting grooves 1511, 1541 such that the multiple fitting pieces 1521, 1522 can move in and out of the multiple fitting grooves 1511, 1541, respectively, in the width directions of the storage portion 1500.

The multiple air passage holes 1523 are holes for effectively refrigerating the pharmaceuticals 300 using the air circulating in the inner case 120, and are provided on both sides (+Y side and −Y side) of the recess 1524 of the side plate 1520.

The recess 1524 has a recessed shape where the flat-plate-shaped antenna 1610 can be fitted, and is formed on a surface of the side plate 1520 on the bottom plate 1510 side (−X side), between the multiple air passage holes 1523. The depth of the recess 1524 (length in the direction along the X-axis) is designed to be greater than the thickness (length in the direction along the X-axis) of the antenna 1610. Accordingly, the antenna 1610 is attached to the side plate 1520 such that an antenna surface of the antenna 1610 on the bottom plate 1510 side (−X side) is recessed from the surface of the side plate 1520 on the bottom plate 1510 side (−X side).

The restriction ribs 1525 are long pieces that restrict movement of the pharmaceuticals 300 toward the side plate 1520 (+X side) to prevent the pharmaceuticals 300 from contacting the side plate 1520, and are integrally formed, at a right-angle corner portion between the bottom plate 1510 and the side plate 1520, along the front-back direction of the storage portion 1500. The shapes of the restriction ribs 1525 may be any shapes as long as the restriction ribs 1525 can restrict movement of the pharmaceuticals 300 toward the side plate 1520. For example, each of exposed surfaces of the restriction ribs 1525 may be a surface tilted toward the bottom plate 1510 as it extends away from the side plate 1520 or a step surface formed of two surfaces that are along the bottom plate 1510 and the side plate 1520, respectively.

Similarly, the restriction rib 1526 is a long piece that restricts movement of the pharmaceuticals 300 toward the back plate 1540 (+Y side) and the side plate 1520 (+X side) to prevent the pharmaceuticals 300 from contacting the back plate 1540 and the side plate 1520, and is integrally formed, at a right-angle corner portion between the back plate 1540 and the side plate 1520, along the height direction of the storage portion 1500. The shape of the restriction rib 1526 may be any shape as long as the restriction rib 1526 can restrict movement of the pharmaceuticals 300 toward the back plate 1540 and the side plate 1520. For example, an exposed surface of the restriction rib 1526 may be a surface tilted toward the back plate 1540 as it extends away from the side plate 1520 or a step surface formed of two surfaces that are along the back plate 1540 and the side plate 1520, respectively.

The recesses 1527 are formed on a surface of the side plate 1520, opposite (+X side) to the surface on which the recess 1524 is formed and facing the multiple air passage holes 1523, on both sides (+Y side and −Y side) of the recess 1524, to reduce the weight of the side plate 1520.

The reinforcement ribs 1528 are provided integrally in the recesses 1527 to increase the strength of the side plate 1520.

The side plate 1530 has multiple fitting pieces 1531, 1532, multiple air passage holes 1533, restriction ribs 1534, 1535, recesses 1536, and reinforcement ribs 1537.

The multiple fitting pieces 1531 are strip-shaped pieces for sliding the side plate 1530 in the width directions of the storage portion 1500, and are formed to protrude from an end of the side plate 1530 on the bottom plate 1510 side (−Z side) toward the bottom plate 1510 so as to be fitted into the multiple fitting grooves 1512 of the bottom plate 1510. Similarly, the multiple fitting pieces 1532 are strip-shaped pieces for sliding the side plate 1530 in the width directions of the storage portion 1500, and are formed to protrude from an end of the side plate 1530 on the back plate 1540 side (+Y side) toward the back plate 1540 so as to be fitted into the multiple fitting grooves 1542 of the back plate 1540. Note that, for example, guide pieces and guide grooves may be provided on outer peripheral surfaces of the multiple fitting pieces 1531, 1532 and inner peripheral surfaces of the multiple fitting grooves 1512, 1542 such that the multiple fitting pieces 1531, 1532 can move in and out of the multiple fitting grooves 1512, 1542, respectively, in the width directions of the storage portion 1500.

The multiple air passage holes 1533 are holes for effectively refrigerating the pharmaceuticals 300 with the air circulating in the inner case 120, and are provided over the entire surface of the side plate 1530.

The restriction rib 1534 is a long piece that restricts movement of the pharmaceuticals 300 toward the side plate 1530 (−X side) to prevent the pharmaceuticals 300 from contacting the side plate 1530, and is integrally formed, at a right-angle corner portion between the bottom plate 1510 and the side plate 1530, along the front-back direction of the storage portion 1500. The shape of the restriction rib 1534 may be any shape as long as the restriction rib 1534 can restrict movement of the pharmaceuticals 300 toward the side plate 1530. For example, an exposed surface of the restriction rib 1534 may be a surface tilted toward the bottom plate 1510 as it extends away from the side plate 1530 or a step surface formed of two surfaces that are along the bottom plate 1510 and the side plate 1530, respectively.

Similarly, the restriction rib 1535 is a long piece that restricts movement of the pharmaceuticals 300 toward the back plate 1540 (+Y side) and the side plate 1530 (−X side) to prevent the pharmaceuticals 300 from contacting the back plate 1540 and the side plate 1530, and is integrally formed, at a right-angle corner portion between the back plate 1540 and the side plate 1530, along the height direction of the storage portion 1500. The shape of the restriction rib 1535 may be any shape as long as the restriction rib 1535 can restrict movement of the pharmaceuticals 300 toward the back plate 1540 and the side plate 1530. For example, an exposed surface of the restriction rib 1535 may be a surface tilted toward the back plate 1540 as it extends away from the side plate 1530 or a step surface formed of two surfaces that are along the back plate 1540 and the side plate 1530, respectively.

The recesses 1536 are formed over the entire surface (−X side) of the side plate 1530 that does not face the side plate 1520, to reduce the weight of the side plate 1530.

The reinforcement ribs 1537 are provided integrally in the recesses 1536 to increase the strength of the side plate 1530. The shape of the reinforcement ribs 1537 may be any shape as long as the reinforcement ribs 1537 can increase the strength of the side plate 1530. For example, the reinforcement ribs 1537 may have a lattice shape.

Four link pieces 1713 to 1716 are long pieces that are provided on the lower side (on the −Z side) of the bottom plate 1510 to work in conjunction with the link pieces 1711, 1712 provided on the upper side (on the +Z side) of the bottom plate 1510 when the side plates 1520, 1530 are slid in the width directions of the storage portion 1500. In this configuration, the link piece 1711 is provided on the side close to the back plate 1540 (+Y side) and the link piece 1712 is provided on the side away from the back plate 1540 (−Y side). The ends on one side of the link pieces 1713, 1714 are pivotably joined to one end of the link piece 1711 on the side away from the back plate 1540 (−Y side), through the slide hole 1513. The end on the other side of the link piece 1713 is pivotably joined to a distal end of the fitting piece 1521 closest to the back plate 1540 among the multiple fitting pieces 1521 of the side plate 1520. The end on the other side of the link piece 1714 is pivotably joined to a distal end of the fitting piece 1531 closest to the back plate 1540 among the multiple fitting pieces 1531 of the side plate 1530. Meanwhile, the ends on one side of the link pieces 1715, 1716 are pivotably joined to one end of the link piece 1712 on the side close to the back plate 1540 (+Y side), through the slide hole 1513. The end on the other side of the link piece 1715 is pivotably joined to a distal end of the fitting piece 1521 farthest from the back plate 1540 among the multiple fitting pieces 1521 of the side plate 1520. The end on the other side of the link piece 1716 is pivotably joined to a distal end of the fitting piece 1531 farthest from the back plate 1540 among the multiple fitting pieces 1531 of the side plate 1530. This enables the side plates 1520, 1530 to slide in directions in which the width of the storage portion 1500 increases while being equidistant from the antenna 1620.

The antennas 1610, 1620 are devices configured to transmit radio waves in the storage portion 1500 to activate the IC chip in the IC tag 310 attached to each pharmaceutical 300, and receive the ID information indicating the pharmaceutical 300. The ID information received by the antennas 1610, 1620 is managed by the controller described later in association with the information on the refrigeration temperature and the put-in and take-out time points of the pharmaceutical 300. The antennas 1610, 1620 are attached so as to be recessed from the side plate 1520 and the back plate 1540, respectively, by using screws and/or the like.

Since the antennas 1610, 1620 are attached so as to be recessed from the side plate 1520 and the back plate 1540, respectively, as described above, the antennas 1610, 1620 do not contact the pharmaceutical 300, thereby being able to reliably receive the ID information indicating the pharmaceutical 300 from the IC tag 310.

In addition, since the restriction ribs 1525, 1526, 1534, 1535, 1544 are provided, the antennas 1610, 1620, the side plates 1520, 1530, and the back plate 1540 do not contact the IC tag 310 attached to the pharmaceutical 300, and thus the antennas 1610, 1620 are able to reliably receive the ID information indicating the pharmaceutical 300 from the IC tag 310. Note that, in this case, the antennas 1610, 1620 may be attached to be flush with the side plate 1520 and the back plate 1540, respectively.

In addition, the provision of the reinforcement ribs 1528, 1537 increases the strength of the side plates 1520, 1530 while reducing the weight of the side plates 1520, 1530, thereby being able to reliably slide the side plates 1520, 1530 with respect to the bottom plate 1510 and the back plate 1540.

In addition, when the width of the storage portion 1500 is increased, the multiple fitting pieces 1521, 1522, 1531, 1532 move away from the multiple fitting holes 1511, 1541, 1512, 1542, thereby forming openings, respectively. These openings serve as air passage holes, to thereby ensure further desirable ventilation for the storage portion 1500.

===Pharmaceutical Management System===

Figure 22:
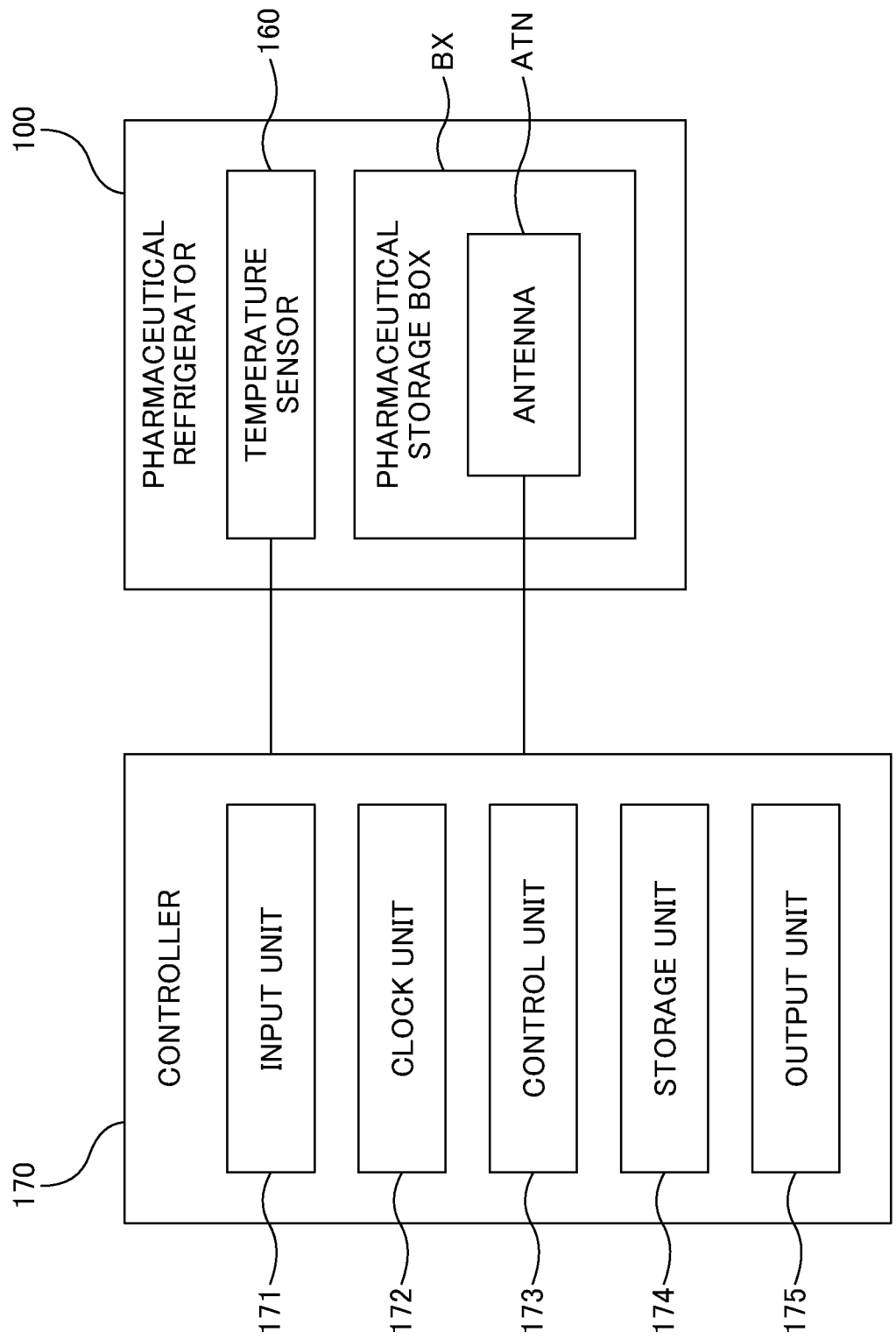
FIG. 22 is a block diagram illustrating an example of a pharmaceutical management system that uses a pharmaceutical storage box according to an embodiment of the present disclosure.

FIG. 22 is a block diagram illustrating an example of a pharmaceutical management system that uses the pharmaceutical storage box according to an embodiment of the present disclosure. For convenience, the pharmaceutical storage boxes according to the first to thirteenth examples are referred to as BX and the antennas according to the first to thirteenth examples are referred to as ATN.

A pharmaceutical management system 1 is a system configured to manage the ID information indicating the pharmaceuticals 300 stored in the pharmaceutical storage box BX stored in the pharmaceutical refrigerator 100 while associating the ID information with information on the refrigeration temperature in the pharmaceutical refrigerator 100 and information on putting-in and taking-out of the pharmaceutical 300.

The pharmaceutical management system 1 is configured such that a controller 170 is communicably coupled to a temperature sensor 160 in the pharmaceutical refrigerator 100 and the antenna ATN attached to the pharmaceutical storage box BX.

The controller 170 includes an input unit 171, a clock unit 172, a control unit 173, a storage unit 174, and an output unit 175.

The input unit 171 receives the information on the temperature in the pharmaceutical refrigerator 100 from the temperature sensor 160 and receives the ID information indicating each pharmaceutical 300 from the antenna ATN.

The clock unit 172 keeps track of the current time.

The control unit 173 periodically obtains the ID information indicating the pharmaceutical 300 from the antenna ATN. For example, when the control unit 173 obtains the ID information indicating the pharmaceutical 300 from the antenna ATN for the first time, the control unit 173 determines that this pharmaceutical 300 has been put into the pharmaceutical refrigerator 100, and regards the current time at this point as the time point when the pharmaceutical 300 has been put into the pharmaceutical refrigerator 100. In addition, when the control unit 173 can no longer obtain the ID information indicating this pharmaceutical 300 from the antenna ATN, the control unit 173 determines that the pharmaceutical 300 has been taken out of the pharmaceutical refrigerator 100, and regards the current time at this point as the time point when the pharmaceutical 300 has been taken out of the pharmaceutical refrigerator 100. Then, the control unit 173 performs a process of associating the ID information of the pharmaceutical 300 with the information on the temperature in the pharmaceutical refrigerator 100 and the information on the put-in and take-out time points of the pharmaceutical 300.

The storage unit 174 stores pieces of the information associated by the control unit 173.

The output unit 175 outputs the associated pieces of the information in response to an instruction from the outside.

Note that a function of the control unit 173 is implemented by executing a program stored in the storage unit 174.

The pharmaceutical(s) 300 and the storage box BX storing the pharmaceutical(s) 300 can be managed accordingly.

The above embodiments of the present disclosure are simply to facilitate understanding of the present disclosure and are not in any way to be construed as limiting the present disclosure. The present disclosure may variously be changed or altered without departing from its essential features and encompass equivalents thereof.

What is claimed is:

1. A pharmaceutical storage box to be stored in a pharmaceutical refrigerator and managed by a controller, the pharmaceutical storage box comprising:
    a storage portion to store a pharmaceutical, the pharmaceutical having an IC tag attached thereto; and
    an antenna configured to receive information of the IC tag,
    wherein the antenna is attached to at least one of a plurality of flat plates, the plurality of flat plates defining the storage portion, and
    wherein the antenna is attached to the at least one of the flat plates such that an antenna surface of the antenna on a side facing the storage portion does not protrude from a surface of the at least one of the flat plates on the side facing the storage portion.

2. The pharmaceutical storage box according to claim 1, wherein the antenna is attached to the at least one of the flat plates such that the antenna surface of the antenna on the side facing the storage portion is recessed from the surface of the at least one of the flat plates on the side facing the storage portion.

3. The pharmaceutical storage box according to claim 1, wherein the antenna includes:
    a first antenna attached to a first flat plate among the plurality of flat plates defining the storage portion, and
    a second antenna attached to a second flat plate among the plurality of flat plates, the second flat plate being perpendicular to the first flat plate.

4. The pharmaceutical storage box according to claim 3, further comprising
    first and second restriction members that restrict movements of the pharmaceutical toward the first and second flat plates, respectively, such that the IC tag does not contact any antenna surface or the plurality of flat plates defining the storage portion when the pharmaceutical is stored in the storage portion.

5. The pharmaceutical storage box according to claim 3, wherein
the first flat plate is a back plate, and
the second flat plate is a side plate.

6. The pharmaceutical storage box according to claim 3, further comprising a coupling portion to couple the first and second antennas to the controller.

7. The pharmaceutical storage box according to claim 1, wherein at least one of the plurality of flat plates defining the storage portion includes a member that shields a radio wave.

8. The pharmaceutical storage box according to claim 7, wherein the member that shields a radio wave has an uneven shape on an inner surface facing the storage portion.

9. The pharmaceutical storage box according to claim 1, wherein a bottom plate on which the pharmaceutical is to be placed among the plurality of flat plates defining the storage portion is tilted relative to a position perpendicular to the antenna surface of the antenna.

10. The pharmaceutical storage box according to claim 1, wherein a top plate among the plurality of flat plates defining the storage portion is configured to be detachably attachable to a plurality of side plates.

11. The pharmaceutical storage box according to claim 1, wherein the pharmaceutical comprising a plurality of pharmaceuticals, and the plurality of pharmaceuticals are to be stored in the storage portion.

12. The pharmaceutical storage box according to claim 11, further comprising a partition plate to partition the storage portion into sections such that the plurality of pharmaceuticals can be stored in the storage portion.

13. The pharmaceutical storage box according to claim 12, wherein the partition plate is configured to be detachably attachable to the storage portion such that positions or volumes of the sections can be changed.

14. The pharmaceutical storage box according to claim 1, further comprising
a tray to store the pharmaceutical, the tray being configured to be stored in the storage portion so as to be insertably removable therefrom.

15. The pharmaceutical storage box according to claim 14, wherein a bottom plate of the tray is tilted relative to a position perpendicular to an antenna surface of the antenna.

16. The pharmaceutical storage box according to claim 14, further comprising a partition plate to partition the tray into sections such that the plurality of pharmaceuticals can be stored in the tray.

17. The pharmaceutical storage box according to claim 16, wherein the partition plate is configured to be detachably attachable to the tray such that positions or volumes of the sections can be changed.

18. The pharmaceutical storage box according to claim 1, wherein the pharmaceutical storage box comprises a plurality of pharmaceutical storage boxes, and the plurality of pharmaceutical storage boxes are to be stored in the pharmaceutical refrigerator, and managed by the single controller.

19. A pharmaceutical storage box to be stored in a pharmaceutical refrigerator and managed by a controller, the pharmaceutical storage box comprising:
a storage portion to store a pharmaceutical, the pharmaceutical having an IC tag attached thereto;
an antenna configured to receive information of the IC tag, wherein the antenna is attached to at least one of a plurality of flat plates, the plurality of flat plates defining the storage portion; and
a restriction member that restricts movement of the pharmaceutical toward the at least one of the flat plates such that the IC tag does not contact an antenna surface or the plurality of flat plates defining the storage portion when the pharmaceutical is stored in the storage portion.

20. A pharmaceutical storage box to be stored in a pharmaceutical refrigerator and managed by a controller, the pharmaceutical storage box comprising:
a storage portion to store a pharmaceutical, the pharmaceutical having an IC tag attached thereto; and
an antenna configured to receive information of the IC tag,
wherein the antenna is attached to at least one of a plurality of flat plates, the plurality of flat plates defining the storage portion,
wherein the antenna includes:
a first antenna attached to a first flat plate among the plurality of flat plates defining the storage portion, and
a second antenna attached to a second flat plate among the plurality of flat plates, the second flat plate being perpendicular to the first flat plate, and
the first antenna is attached to the first flat plate such that an antenna surface of the first antenna on a side facing the storage portion does not protrude from a surface of the first flat plate on the side facing the storage portion, and
the second antenna is attached to the second flat plate such that an antenna surface of the second antenna on the side facing the storage portion does not protrude from a surface of the second flat plate on the side facing the storage portion.

21. The pharmaceutical storage box according to claim 20, wherein
the first antenna is attached to the first flat plate such that the antenna surface of the first antenna on the side facing the storage portion is recessed from the surface of the first flat plate on the side facing the storage portion, and
the second antenna is attached to the second flat plate such that the antenna surface of the second antenna on the side facing the storage portion is recessed from the surface of the second flat plate on the side facing the storage portion.

22. A pharmaceutical storage box to be stored in a pharmaceutical refrigerator and managed by a controller, the pharmaceutical storage box comprising:
a storage portion to store a pharmaceutical, the pharmaceutical having an IC tag attached thereto; and
an antenna configured to receive information of the IC tag,
wherein the antenna is attached to at least one of a plurality of flat plates, the plurality of flat plates defining the storage portion, and
wherein the plurality of flat plates includes flat plates each including:
a recessed portion formed such that a flat plate surface opposite to a flat plate surface facing the storage portion is recessed; and
a reinforcement member that fits in the recessed portion.

23. The pharmaceutical storage box according to claim 22, wherein the reinforcement member has a lattice shape.

24. A pharmaceutical storage box to be stored in a pharmaceutical refrigerator and managed by a controller, the pharmaceutical storage box comprising:
a storage portion to store a pharmaceutical, the pharmaceutical having an IC tag attached thereto; and an antenna configured to receive information of the IC tag,
wherein at least one of a plurality of flat plates defining the storage portion is configured to be slidable with respect to another flat plate such that a volume of an inside of the storage portion can be changed.

* * * * *